United States Patent
Kveen et al.

(10) Patent No.: US 6,945,993 B2
(45) Date of Patent: Sep. 20, 2005

(54) STENT

(75) Inventors: Craig L. Kveen, Maple Grove, MN (US); Timothy G. J. Ehr, Elk River, MN (US); Brian J. Brown, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 197 days.

(21) Appl. No.: 10/287,286

(22) Filed: Nov. 4, 2002

(65) Prior Publication Data

US 2003/0055489 A1 Mar. 20, 2003

Related U.S. Application Data

(60) Continuation of application No. 09/904,635, filed on Jul. 13, 2001, now Pat. No. 6,478,816, which is a division of application No. 09/111,531, filed on Jul. 8, 1998, now Pat. No. 6,261,319.

(51) Int. Cl.[7] .................................................. A61F 2/06
(52) U.S. Cl. ...................................................... 623/1.15
(58) Field of Search ................................ 623/1.11–1.15

(56) References Cited

U.S. PATENT DOCUMENTS

| | | | |
|---|---|---|---|
| 5,102,417 A | 4/1992 | Palmaz | 606/195 |
| 5,449,373 A | 9/1995 | Pinchasik et al. | 606/198 |

(Continued)

FOREIGN PATENT DOCUMENTS

| | | |
|---|---|---|
| DE | 297 01 758 | 5/1997 |
| DE | 297 02 671 U1 | 5/1997 |
| DE | 297 08 689 U1 | 8/1997 |
| DE | 297 08 879 U1 | 9/1997 |
| DE | 297 16 476 U1 | 2/1998 |
| EP | 0 734 698 A2 | 2/1996 |
| EP | 0 875 215 A1 | 11/1998 |
| FR | 2 785 174 | 5/2000 |
| WO | 96/03092 | 2/1996 |
| WO | 97/04721 | 2/1997 |
| WO | 97/14375 | 4/1997 |
| WO | 97/25937 | 7/1997 |
| WO | 97/26840 | 7/1997 |
| WO | 97/32543 | 9/1997 |
| WO | 97/32544 | 9/1997 |

(Continued)

OTHER PUBLICATIONS

U.S. Appl. No. 09/904,635, filed Jul.13, 2001, Kveen et al.
U.S. Appl. No. 09/111,531, filed Jul. 8, 1998, Kveen et al.
Handbook of Coronary Stents, Second Edititon, Edited by Patrick W. Serruys and Michael J.B. Kutryk, 1998 publication by Mosby, pp. 157–170, 229–234.
Carbostent™ Carbofilm ™ Coated Coronary Stent System, Sorin Biomedia.

*Primary Examiner*—Suzette J-J Gherbi
(74) *Attorney, Agent, or Firm*—Vidas, Arrett & Steinkraus, P.A.

(57) ABSTRACT

A radially expandable stent comprising a plurality of spaced band-like elements and intersecting links is disclosed. The band-like elements have a generally serpentine configuration to provide continuous waves of generally sinusoidal character to each band-like element. The waves are characterized by a plurality of peaks and troughs taking a generally longitudinal direction along the cylinder such that the waves in the band-like elements open as the stent is expanded from a first diameter to a second diameter. The intersecting links are substantially U-shaped and terminate in first and second shanks. The first shank of a link emanates from a region between a peak and trough on a band-like element and the second shank of the link emanates from a region between a peak and trough on an adjacent band-like element.

7 Claims, 26 Drawing Sheets

U.S. PATENT DOCUMENTS

| | | | |
|---|---|---|---|
| 5,591,197 A | 1/1997 | Orth et al. | 606/198 |
| 5,695,516 A | 12/1997 | Fischell et al. | 606/194 |
| 5,697,971 A | 12/1997 | Fischell et al. | 623/1 |
| 5,718,713 A | 2/1998 | Frantzen | 606/198 |
| 5,733,303 A | 3/1998 | Israel et al. | 606/198 |
| 5,735,893 A | 4/1998 | Lau et al. | 623/1 |
| 5,741,327 A | 4/1998 | Frantzen | 623/1 |
| 5,755,776 A | 5/1998 | Al-Saadon | 623/1 |
| 5,755,781 A | 5/1998 | Jayaraman | 623/1 |
| 5,776,161 A | 7/1998 | Globerman | 606/194 |
| 5,776,183 A | 7/1998 | Kanesaka et al. | 623/1 |
| 5,807,404 A * | 9/1998 | Richter | 623/1 |
| 5,810,872 A * | 9/1998 | Kanesaka et al. | 623/1 |
| 5,827,321 A * | 10/1998 | Roubin et al. | 606/195 |
| 5,855,600 A * | 1/1999 | Alt | 623/1 |
| 5,868,781 A * | 2/1999 | Killion | 623/1 |
| 5,911,754 A * | 6/1999 | Kanesaka et al. | 623/1.15 |
| 5,922,021 A * | 7/1999 | Jang | 623/1.15 |
| 5,948,016 A * | 9/1999 | Jang | 623/1.15 |
| 5,954,743 A | 9/1999 | Jang | 606/198 |
| 6,033,433 A * | 3/2000 | Ehr et al. | 623/1.15 |
| 6,053,940 A | 4/2000 | Wijay | 623/1 |
| 6,066,169 A | 5/2000 | McGuinness | 623/1.16 |
| 6,068,656 A * | 5/2000 | Von Oepen | 623/1.17 |
| 6,090,127 A | 7/2000 | Globerman | 606/194 |
| 6,099,455 A * | 8/2000 | Columbo et al. | 600/3 |
| 6,113,627 A * | 9/2000 | Jang | 623/1.5 |
| 6,117,165 A | 9/2000 | Becker | 623/1 |
| 6,123,721 A | 9/2000 | Jang | 623/1 |
| 6,193,747 B1 * | 2/2001 | von Oepen | 623/1.15 |
| 6,203,569 B1 | 3/2001 | Wijay | 623/1.15 |
| 6,261,319 B1 * | 7/2001 | Kveen et al. | 623/1.15 |
| 6,325,821 B1 | 12/2001 | Gaschino et al. | 623/1.15 |
| 6,330,884 B1 | 12/2001 | Kim | 128/898 |
| 6,352,552 B1 * | 3/2002 | Levinson et al. | 623/1.15 |
| 6,461,380 B1 * | 10/2002 | Cox | 623/1.17 |
| 6,478,816 B1 | 11/2002 | Kveen et al. | |
| 2003/0149469 A1 | 8/2003 | Wolinsky et al. | 623/1.11 |

FOREIGN PATENT DOCUMENTS

| | | | |
|---|---|---|---|
| WO | 97/33534 | 9/1997 | |
| WO | WO 97/33534 * | 9/1997 | 623/1.15 |
| WO | 97/40780 | 11/1997 | |
| WO | 97/40783 | 11/1997 | |
| WO | 98/18405 | 3/1998 | |
| WO | 98/20927 | 5/1998 | |
| WO | 98/22159 | 5/1998 | |
| WO | 02/091958 | 11/2002 | |

* cited by examiner

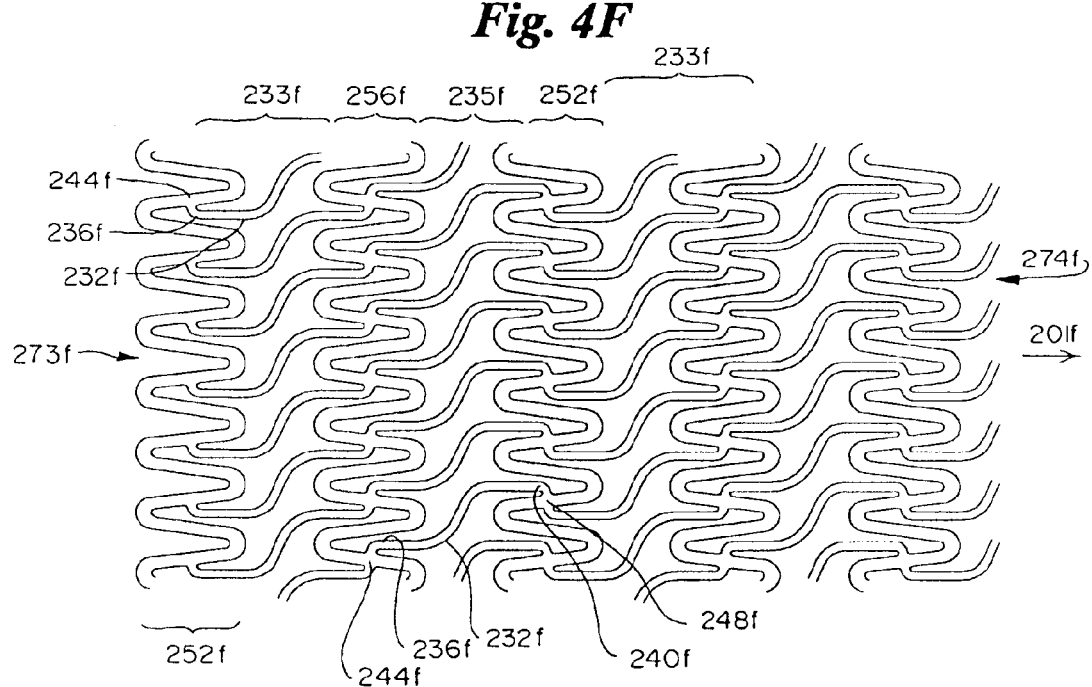

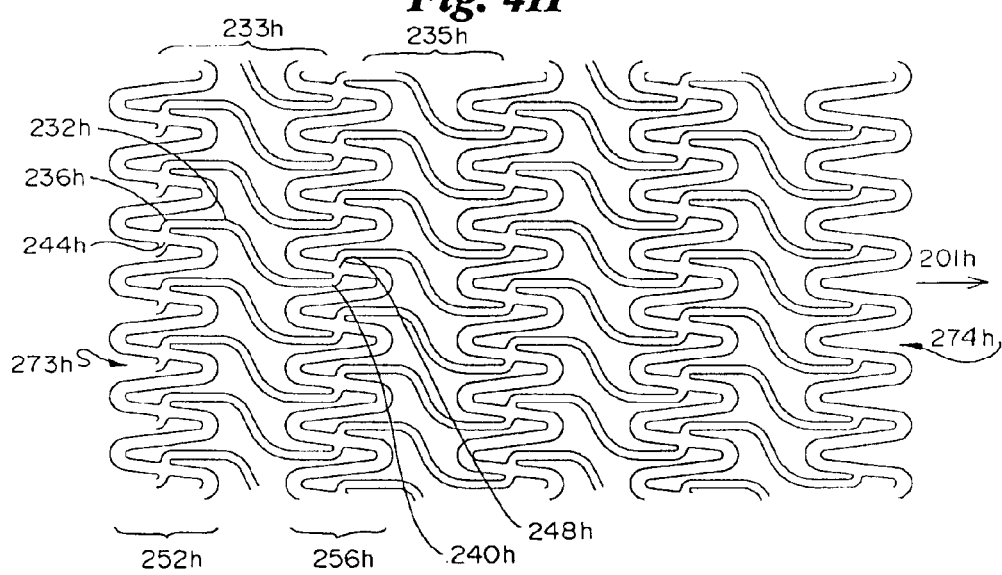

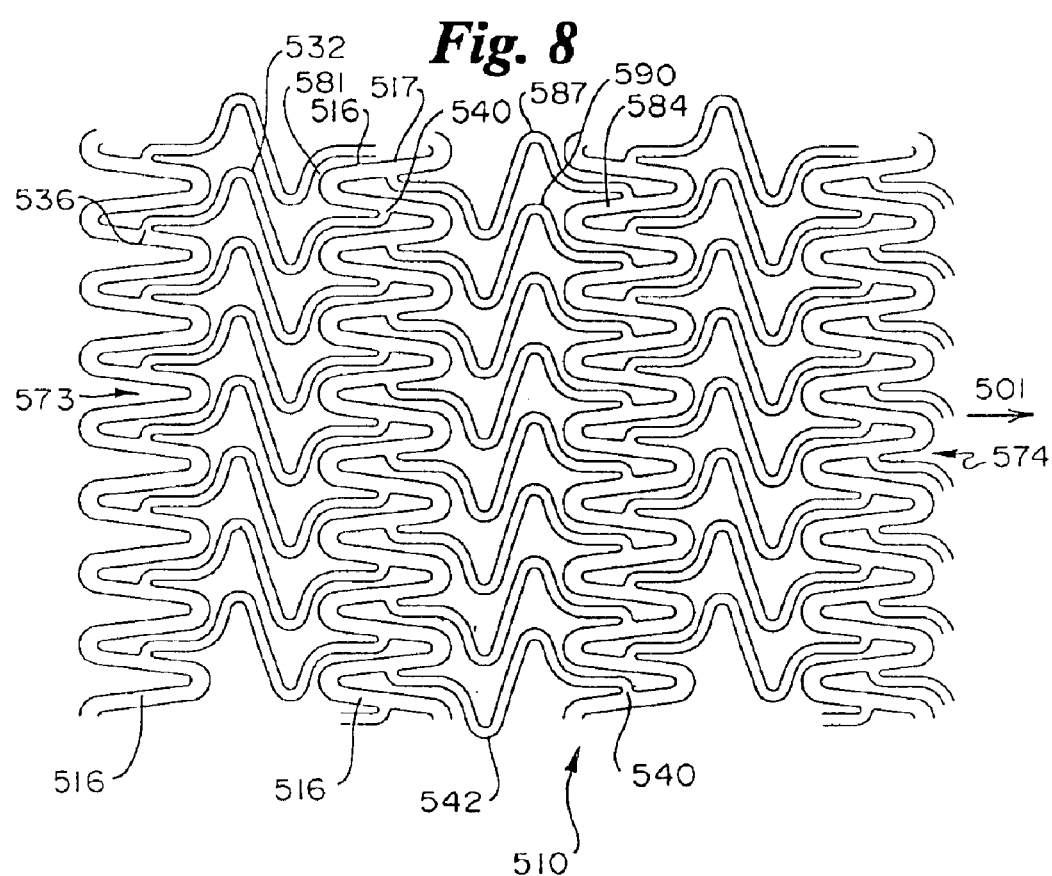

STENT

This application is a Continuation application of application Ser. No. 09/904,635 filed Jul. 13, 2001 is now U.S. Pat. No. 6,478,816 which is a Divisional application of application Ser. No. 09/111,531 filed Jul. 8, 1998 now U.S. Pat. No. 6,261,319, the contents of which are hereby incorporated by reference.

FIELD OF THE INVENTION

This invention relates to an endoprosthesis device for implantation within a body vessel, typically a blood vessel. More specifically, it relates to a tubular expandable stent of improved longitudinal flexibility.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in the urinary tract and in bile ducts.

Typically, a stent will have an unexpanded (closed) diameter for placement and an expanded (opened) diameter after placement in the vessel or the duct. Some stents are self-expanding and some are expanded mechanically with radial outward force from within the stent, as by inflation of a balloon.

An example of the latter type is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

This invention is directed to stents of all these types when configured so as to be longitudinally flexible as described in detail hereinbelow. Flexibility is a desirable feature in a stent so as to conform to bends in a vessel. Such stents are known in the prior art. Examples are shown in U.S. Pat. No. 4,856,516 to Hillstead; U.S. Pat. No. 5,104,404 to Wolff; U.S. Pat. No. 4,994,071 to MacGregor; U.S. Pat. No. 5,102,417 to Palmaz; U.S. Pat. No. 5,195,984 to Schatz; U.S. Pat. No. 5,135,536 to Hillstead; U.S. Pat. 5,354,309 to Shepp-Pesch et al.; EPO Patent Application 0 540 290 A2 to Lau; EPO Patent Application No. 0 364 787 B1 to Schatz, and PCT Application WO 94/17754 (also identified as German Pat. Application 43 03 181).

Generally speaking, these kinds of stents are articulated and are usually formed of a plurality of aligned, expandable, relatively inflexible, circular segments which are interconnected by flexible elements to form a generally tubular body which is capable of a degree of articulation or bending. Unfortunately, a problem with such stents is that binding, overlapping or interference can occur between adjacent segments on the inside of a bend due to the segments moving toward each other and into contact. Moreover, on the outside of a bend, the segments can move away from each other, leaving large gaps. This can lead to improper vessel support, vessel trauma, flow disturbance, kinking, balloon burst during expansion, and difficult recross for devices to be installed through already implanted devices and to unsupported regions of vessel.

A diamond configuration with diagonal connections between each and every diamond of each segment is also known but such closed configurations lack flexibility.

Such stents also suffer from the problem of shortening upon radial expansion. As the stent expands radially, it contracts lengthwise.

It is an object of this invention to provide a stent with a distributed structure which is longitudinally flexible that avoids these problems and exhibits improved flexibility in the stent body segments thereof rather than in flexible joints between the segments. It is a further object to provide stents that exhibit a desired lengthening or a desired shortening on radial expansion as well as stents which exhibit substantially no shortening or lengthening on radial expansion.

It is a further object of the present invention to provide a stent formed of a series of interconnected flexible cells.

It should be noted that for the purposes of this invention, the phrase generally sinusoidal is intended to include waves characterized by sine and cosine functions as well as waves which are not rigorously characterized by those functions, but nevertheless resemble such waves. In a more general way, such waves include those which are characterized as having one or more peaks and troughs. As an example, a wave whose peaks and troughs are U shaped or bulbous is intended to be included. Also intended to be included, without limiting the definition, are waves which are more triangular in shape such as a saw-tooth wave or waves whose peaks and troughs are rectangular.

SUMMARY OF INVENTION

The present invention provides a radially expandable stent having first and second ends and a longitudinal axis. The stent comprises a plurality of spaced band-like elements forming a hollow cylinder. The band-like elements are arranged sequentially along the cylinder and each band-like element comprises one or more sub-elements having a generally serpentine configuration to provide continuous waves to each sub-element. The waves are characterized by a plurality of peaks and troughs taking a generally longitudinal direction along the cylinder such that the waves in the sub-elements open as the stent is expanded from a first diameter to a second diameter. Adjacent band-like elements in the stent are connected together by one or more links. Each link has at least one bend therein and terminates in first and second shanks. The first shank of each link emanates from a region of attachment between a peak and trough on a sub-element of a band-like element while the second shank of each link emanates from a region of attachment between a peak and trough on a sub-element of an adjacent band-like element. The first shanks attached to any given sub-element of a band-like element are spaced substantially one wavelength or more apart along the sub-element of a band-like element. Likewise, the second shanks attached to any given sub-element of a band-like element are spaced substantially one wavelength or more apart along the sub-element of the band-like element.

The present invention is also directed to a radially expandable stent comprising a plurality of spaced band-like elements forming a hollow cylinder. The band-like elements are arranged sequentially along the cylinder. Each band-like element has a generally serpentine configuration to provide continuous waves of generally sinusoidal character to each band-like element. The waves are characterized by a plurality of peaks and troughs taking a generally longitudinal direction along the cylinder, the peaks and troughs having a midpoint region midway between them, such that the waves in the band-like elements open as the stent is expanded from a first diameter to a second diameter. The stent further comprises one or more spaced generally longitudinal elements extending from the first end of the stent to the second end of the stent and having alternating peaks and troughs and longitudinal transition regions midway between adjacent peaks and troughs. Adjacent longitudinal elements are in phase with one another. Each generally longitudinal element intersects each band-like element in a region of intersection, which includes a region between a peak and a trough on a band-like element, and a transition region of a longitudinal element. Adjacent longitudinal elements intersect each band-like element at least one wavelength apart along the band-like element.

The present invention is further directed to an expandable stent which in expanded form comprises a plurality of flexible connected primary cells. Each primary cell comprises a first member having first and second ends extending in a direction generally perpendicular to the longitudinal axis of the stent and having a serpentine shape. The first members each have one peak and one trough, the peak and trough taking a generally longitudinal direction along the stent. Each primary cell further comprises a second member having first and second ends extending in a direction generally perpendicular to the longitudinal axis, and having a serpentine shape. The second members have one peak and one trough, the peak and trough taking a generally longitudinal direction along the stent. The second member is situated generally opposite the first member and is optionally out of phase with the first member. The primary cells also comprise a first link having a first end and a second end, and extending in a generally longitudinal direction. The first link has at least one bend therein and is disposed between the first end of the first member and the first end of the second member. The first end of the first link is attached to the first end of the first member and the second end of the first link is attached to the first end of the second member. Finally, each primary cell comprises a second link having a first end and a second end, extending in a generally longitudinal direction. The second link has at least one bend therein and is disposed between the second end of the first member and the second end of the second member. The first end of the second link is attached to second end of the first member and the second end of the second link is attached to the second end of the second member. The second link is in phase with the first link. The primary cells are arranged in one or more primary bands and adjacent primary bands are interconnected. Primary cells in adjacent bands may optionally be offset relative to one another along the bands.

Optionally, the stent may further comprise secondary bands comprised of secondary cells, the secondary bands alternating with the primary bands.

BRIEF DESCRIPTION OF THE FIGURES

FIG. 4f shows a flat view of an alternate unexpanded stent configuration according to the invention.

FIG. 4h shows a flat view of an alternate unexpanded stent configuration according to the invention.

FIG. 5 shows an enlarged view of the circled region in FIG. 4a.

FIG. 6b shows an expanded stent of the configuration shown in FIG. 6a.

FIG. 7b shows an expanded stent of the configuration shown in FIG. 7a.

FIG. 8 shows a flat view of an alternate unexpanded stent configuration according to the invention.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the sake of consistency, the terms 'peak' and 'trough' shall be defined with respect to the proximal and distal ends of the stent. As seen in the Figures, each of the stents has a proximal end designated by a numeral ending in 73 (e.g., 173) and a distal end designated by a numeral ending in 74 (e.g. 174). Peaks are concave relative to the proximal end of the stent and convex relative to the distal end of the stent. Troughs, on the other hand, are convex relative to the proximal end of the stent and concave relative to the distal end of the stent.

Figure 1:
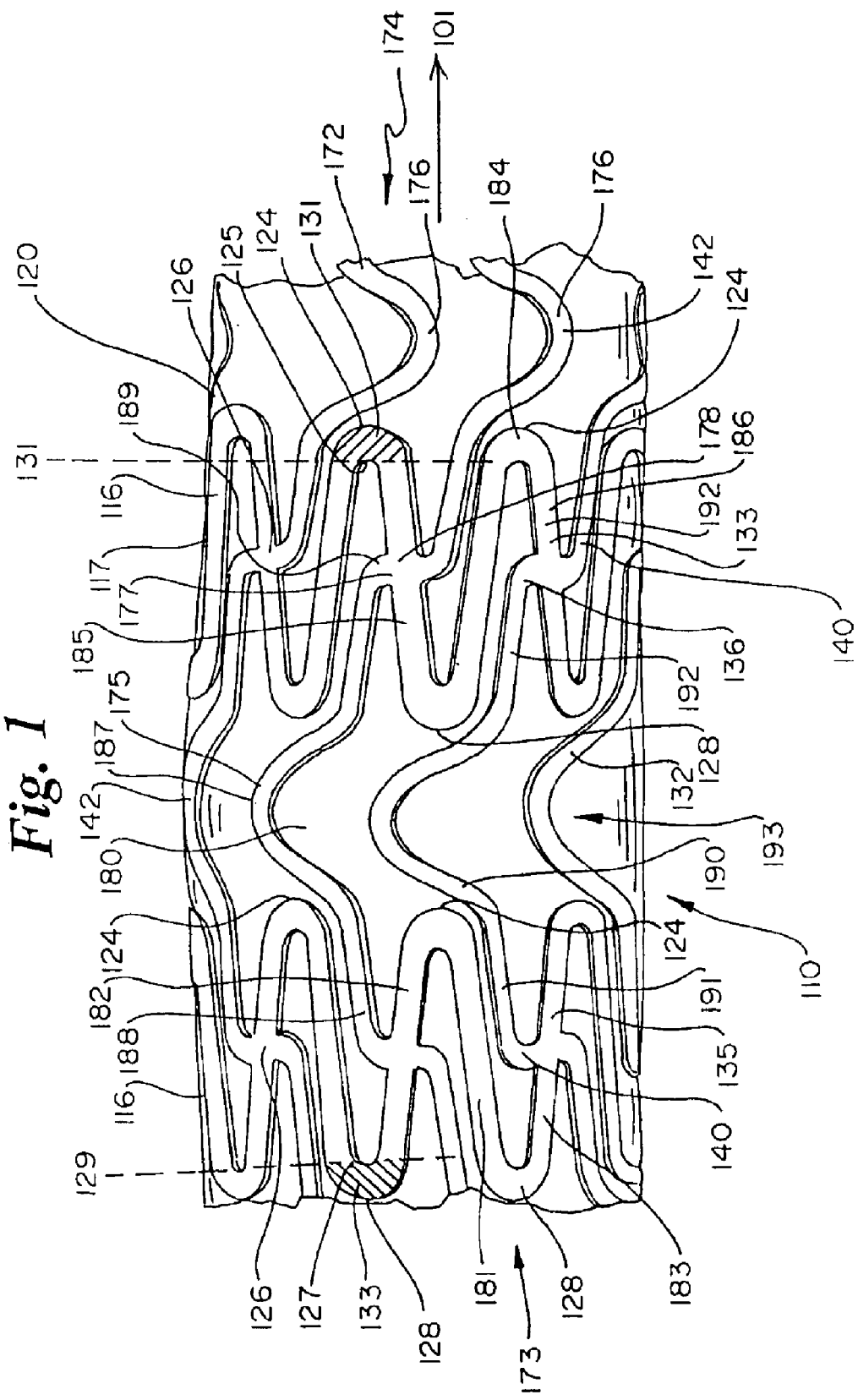
FIG. 1 shows a tubular, unexpanded stent according to the invention.

Moreover, for the sake of clarity, the terms 'peak' are 'trough' in reference to a band-like element or sub-element are intended to include not only the point(s) of maximum or minimum amplitude on a band-like element, but also a small region around the maximum or minimum. More precisely, in the case of peaks, the 'small region' around the maximum is intended to include any point along the band-like element which is distal of a line extending through the innermost part of the band-like element at the maximum amplitude and perpendicular to the longitudinal axis of the stent up to the peak itself. In the case of troughs, the 'small region' around the minimum is intended to include any point along the band-like element which is proximal of a line extending through the innermost part of the band-like element at the minimum amplitude and perpendicular to the longitudinal axis of the stent up to the trough itself. As seen in FIG. 1, each peak 124 has an innermost part of the peak 125 which lies on the inside of the band-like element opposite the peak and each trough 128 has an innermost part 127. Peak region 131, shaded for illustrative purpose in one instance, is seen to be that region of the band-like element that extends distal to innermost part 125 and line 131 extending through innermost part 125 perpendicular to longitudinal axis 101. Similarly trough region 133 shaded for illustrative purpose in one instance, is seen to be that region of the band-like element that extends proximal to innermost part 127 and line 129 extending through innermost part 127 perpendicular to longitudinal axis 101.

Figure 2:
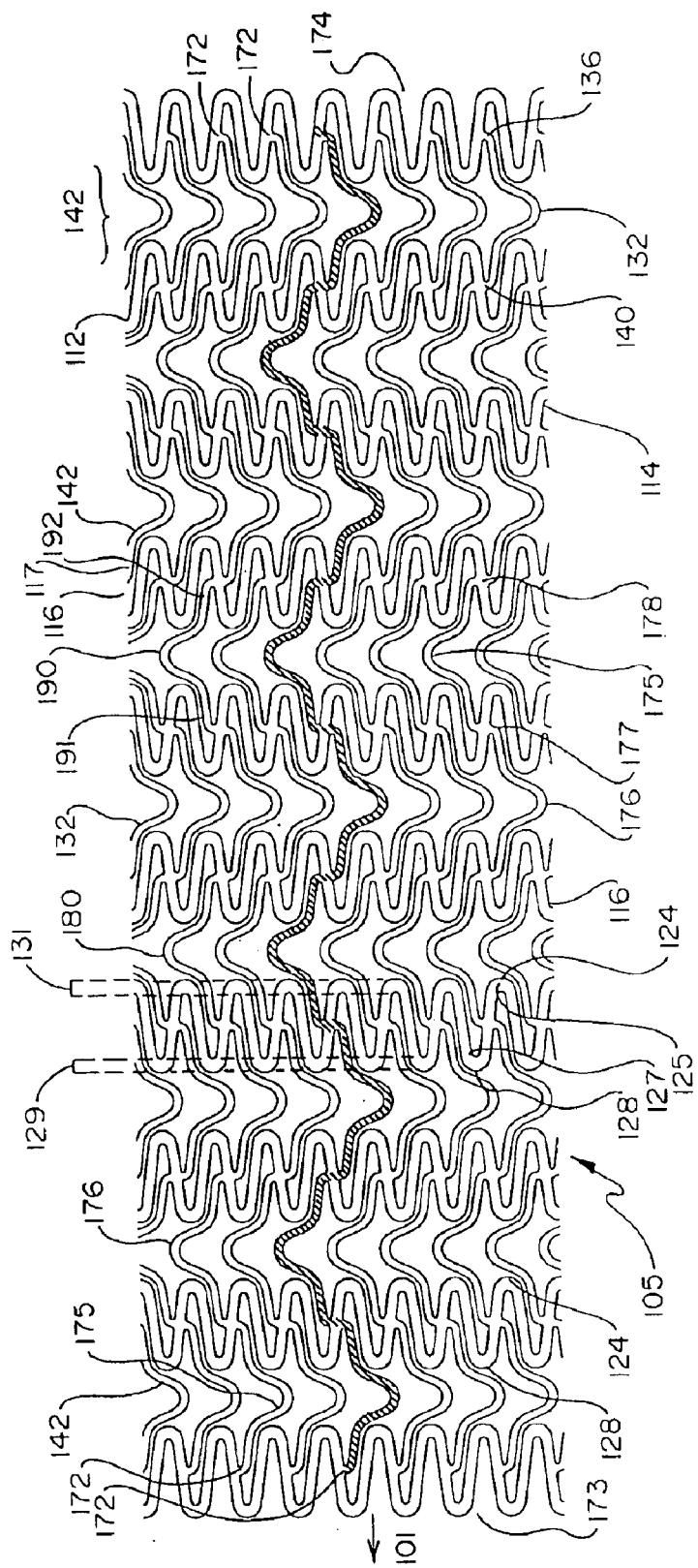
FIG. 2 shows a flat view of the pattern used in the stent shown in FIG. 1.

Turning to the Figures, FIG. 2 shows generally at 105 a fragmentary flat view of an unexpanded stent configuration. An actual inventive tubular stent in unexpanded form is shown generally at 110 in FIG. 1. The stent is shown for clarity in FIG. 2 in the flat and may be made from flat pattern 105, shown generally in FIG. 2, which is formed into a tubular shape by rolling the pattern so as to bring edges 112 and 114 together. The edges may then be joined as by welding or the like to provide a configuration such as that showed in FIG. 1. The stent may also be formed of a laser-cut tube.

The configuration can be seen in these Figures to be made up of a plurality of spaced band-like elements, generally indicated at 116, forming a hollow cylinder 120. Band-like elements 116 comprise one or more sub-elements. In the embodiment shown in FIG. 2, each band-like element 116 is formed of one sub-element 117 although in other embodiments the band-like elements may be formed of multiple sub-elements. Sub-elements 117 are arranged sequentially along cylinder 120, as shown in FIG. 1. Each sub-element 117 has a generally serpentine configuration to provide continuous waves of generally sinusoidal character to each sub element 117, the waves being characterized by a plurality of peaks 124 and troughs 128 taking a generally longitudinal direction along cylinder 120. As the stent is expanded from a first diameter to a second diameter, the waves in sub-elements open.

Figure 3:
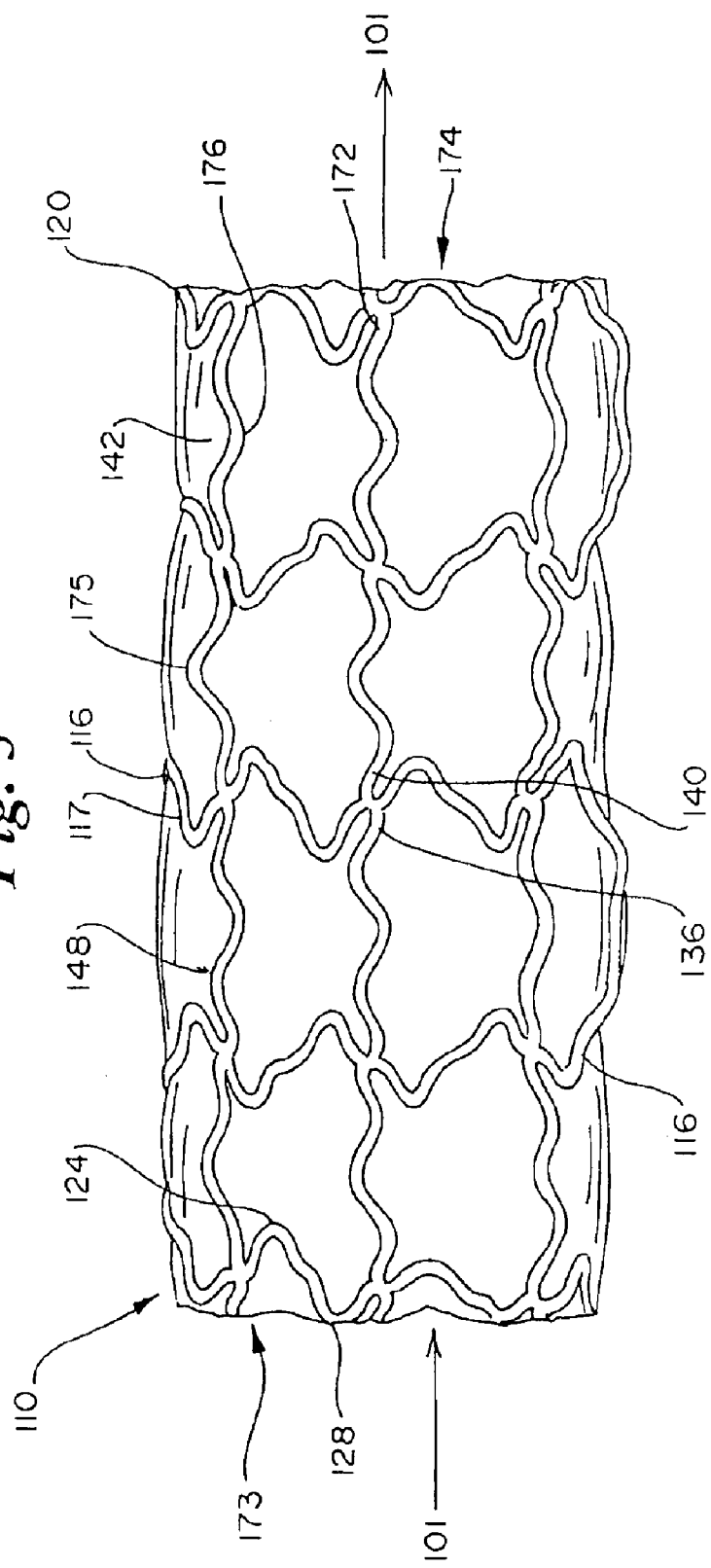
FIG. 3 shows an expanded stent of the configuration shown in FIG. 1.

The inventive stents further comprise a plurality of links, each link having at least one bend therein. In the embodiment of FIG. 2, U-shaped links 132 connect adjacent band-like elements 116 together. Although substantially U-shaped, links 132 may be rounded or square or pointed or the like. As shown in FIGS. 1–3, links 132 extending between adjacent bands 116 are arranged to form rows 142 of links 132. Links in adjacent rows are 180° out of phase with one another. Links 132 terminate in first 136 and second 140 shanks. As shown in FIG. 2, the first shank 136 of a link 132 emanates from a region 133 between a peak 124 and trough 128 on a band-like element 116 and the second shank 140 of the link 132 emanates from a region 135 between a peak 124 and trough 128 on an adjacent band-like element. First shanks 136 attached to any given sub-element of a band-like element are spaced substantially one wavelength apart along the sub-element of the band-like element and similarly, second shanks 140 attached to any given sub-element of a band-like element are spaced substantially one wavelength apart along the sub-element of the band-like element.

Although first shank 136 and second shank 140 are substantially perpendicular to the bands in the region of intersection between the shanks and the bands as depicted in FIGS. 1–2, this is not a requirement of the invention. As such, the first and second shanks may be angled at some other acute angle.

A minimum of one link 132 is required to connect adjacent band-like elements. Preferably, there will be a one-to-one correspondence between links and peaks (or troughs). Of course, any number of links intermediate between 1 and the number requisite for a one-to-one correspondence of peaks (troughs) and links may be used as well to join adjacent band-like elements.

For the sake of completeness, the stent of FIG. 2 is shown generally at 110 in FIG. 3 in its expanded state. As shown in FIG. 3, the 'U' shaped links assume an 'M' shape as a result of the expansion of the stent. The 'M' shaped links are shown at 148.

The stent of FIGS. 1–3 may also be seen to be formed of a plurality of band-like elements 116 and a plurality of spaced generally longitudinal elements 172 (one of which is highlighted for clarity in FIG. 2). As shown in FIG. 2, longitudinal elements 172 extend from the first end 173 of the stent to the second end 174 of the stent and have alternating peaks 175 and troughs 176 and longitudinal transition regions 177 midway between adjacent peaks 175 and troughs 176. Adjacent longitudinal elements 172 are in phase with one another. Each generally longitudinal element 172 intersects each band-like element 116 in a region of intersection 178, the region of intersection including a region between a peak and a trough on a band-like element, and a transition region 177 of a longitudinal element 172.

The stent, as seen in FIGS. 1 and 2, may also seen to be comprised of a plurality of flexible connected primary cells 180. Each primary cell 180 has a first member 181 having first 182 and second 183 ends extending in a direction generally perpendicular to the longitudinal axis. First member 181 has a serpentine shape with one peak 124 and one trough 128. Peak 124 and trough 128 take a generally longitudinal direction along the stent. Each primary cell 180 further has a second member 184 having first 185 and second 186 ends and extending in a direction generally perpendicular to the longitudinal axis. Second member 184 has a serpentine shape and has one peak 124 and one trough 128. Peak 124 and trough 128 take a generally longitudinal direction along the stent. Second member 184 is situated generally opposite first member 181, and is out of phase with first member 181 by 180°. Extending between first member 181 and second member 184 is a first link 187 having a first end 188 and a second end 189. First link 187 extends in a generally longitudinal direction, and has at least one bend therein. First end 188 of first link 187 is attached to first end 182 of first member 181. Second end 189 of first link 187 is attached to first end 185 of second member 184. Finally, extending between first member 181 and second member 184, and parallel to first link 187 is second link 190 having a first end 191 and a second end 192. First end 191 of second link 190 is attached to second end 183 of first member 181 and second end 192 of second link 190 is attached to second end 186 of second member 184. Second link 190 is in phase with first link 187. Primary cells 180 are arranged in one or more primary bands, shown generally at 193 and adjacent primary bands are interconnected.

Although first shank 136 and second shank 140 of links 132 are depicted in FIG. 2 as extending from regions substantially opposite each other on adjacent band-like elements, the regions need not be substantially opposite one another but rather, may be displaced relative to one another on their respective band-like elements. Depending on the circumferential displacement between the first and second shanks of a given link, and the relative phasing of adjacent band-like elements, the first and second shanks will either be oriented substantially in the same direction or substantially in the opposite direction. For the sake of this invention, first shanks 136 and second shanks 140 associated with links 132 as shown in FIG. 2 are considered to be oriented in substantially the same direction. Both shanks are oriented upward.

Figure 4A:
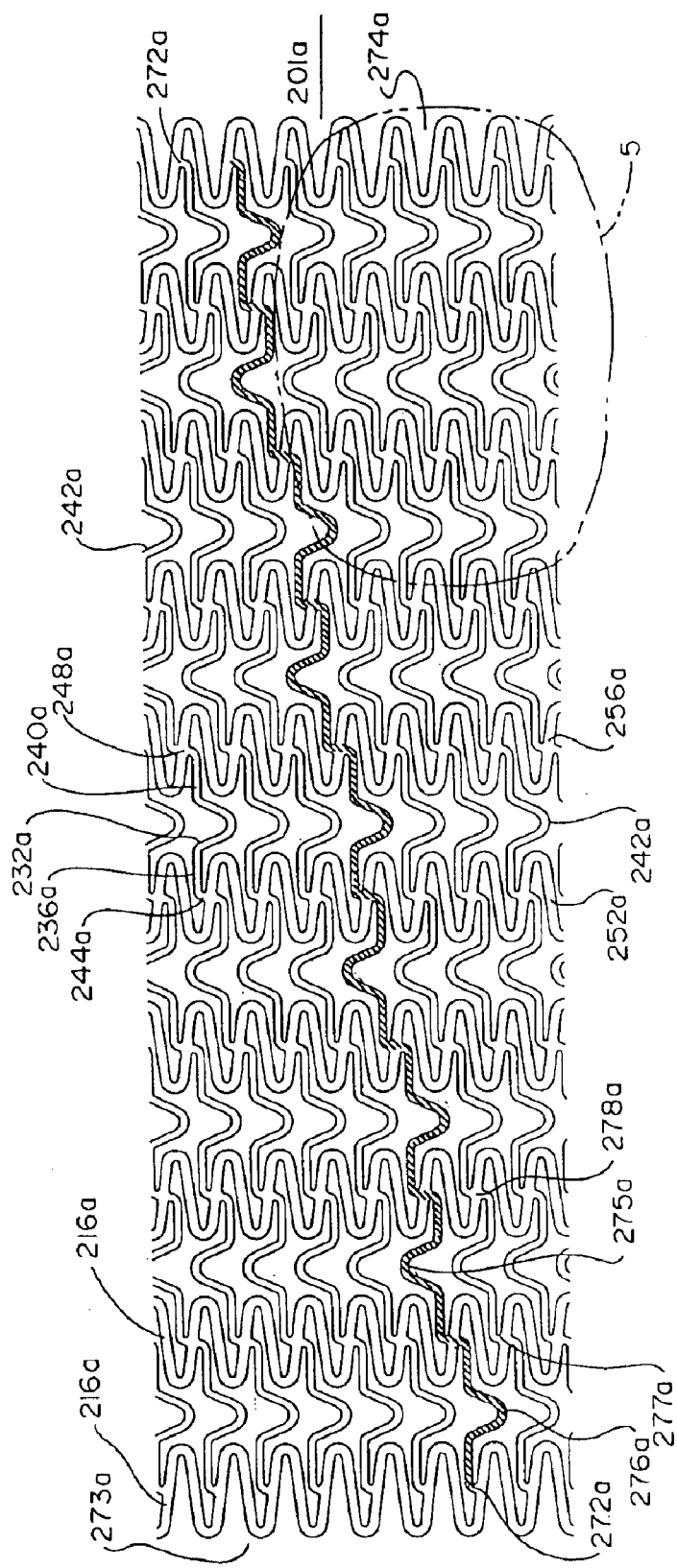
FIG. 4a shows a flat view of an alternate unexpanded stent configuration according to the invention.

In FIG. 4a, on the other hand, first shanks 236a and second shanks 240a of each link 232a are considered to be oriented in substantially opposite directions. One shank is oriented upward while the other shank is oriented downward. In the specific embodiment shown in FIG. 4a, first shank 236a of each link 232a extends from a first region 244a on a first band-like element 252a and second shank 240a of each link 232a extends from a second region 248a on an adjacent band-like element 256a, with second region 248a situated opposite a region one half wavelength further along first band-like element 252a from first region 244a. Of course, the half wavelength separation of FIG. 4a is meant to be exemplary of a more general class of stents in which one shank of a link is oriented upward and one shank of a link is oriented downward. As such, other separations between the regions of attachment of the first and second shanks are contemplated as well.

Figure 4B:
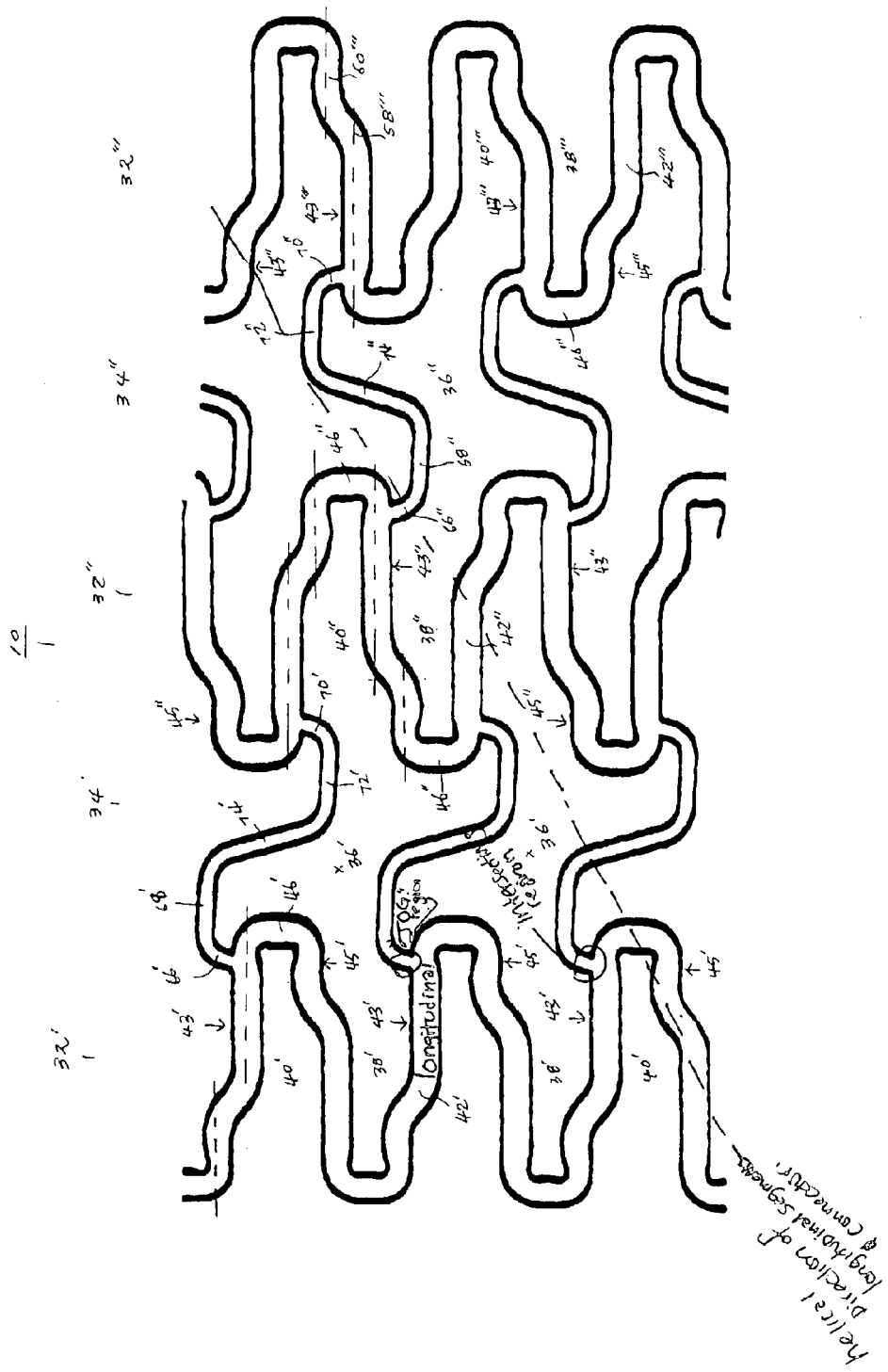
FIG. 4b shows a flat view of an alternate unexpanded stent configuration according to the invention.
Figure 4C:
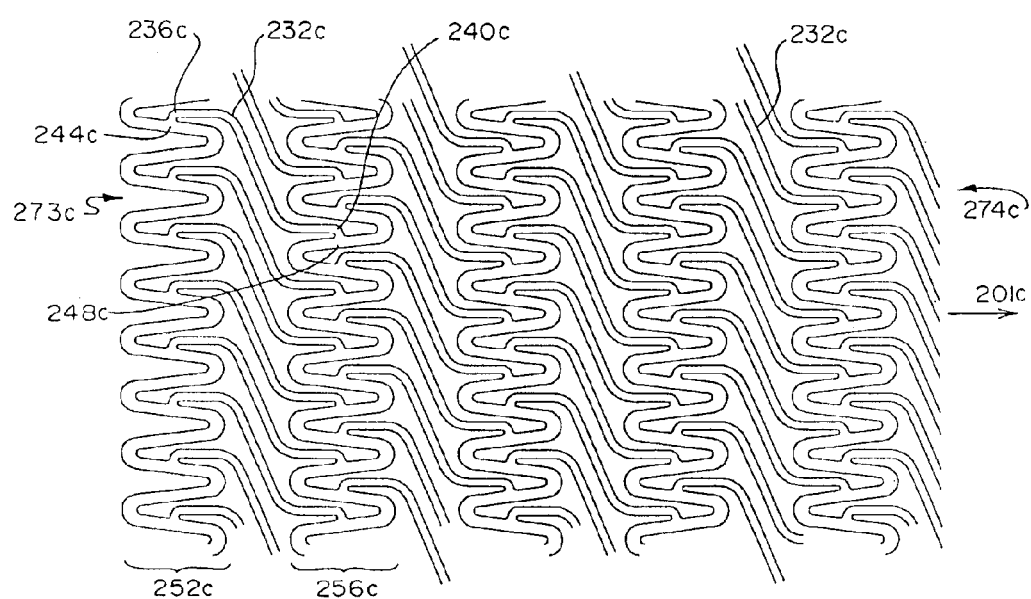
FIG. 4c shows a flat view of an alternate unexpanded stent configuration according to the invention.
Figure 4D:
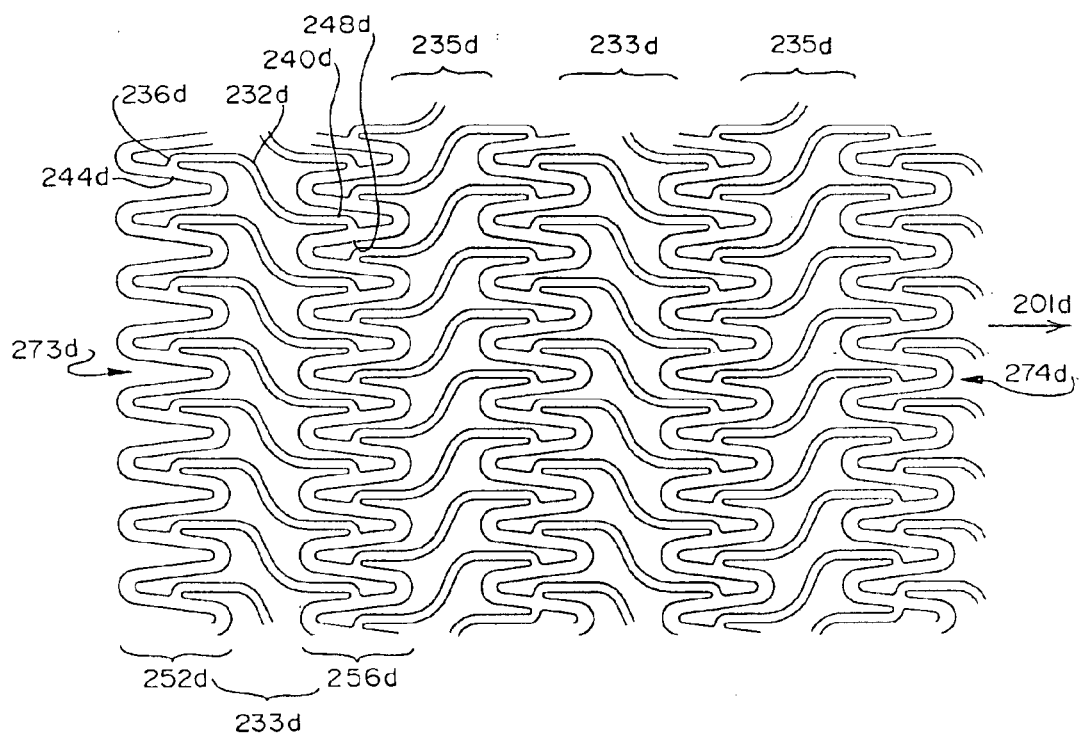
FIG. 4d shows a flat view of an alternate unexpanded stent configuration according to the invention.
Figure 4E:
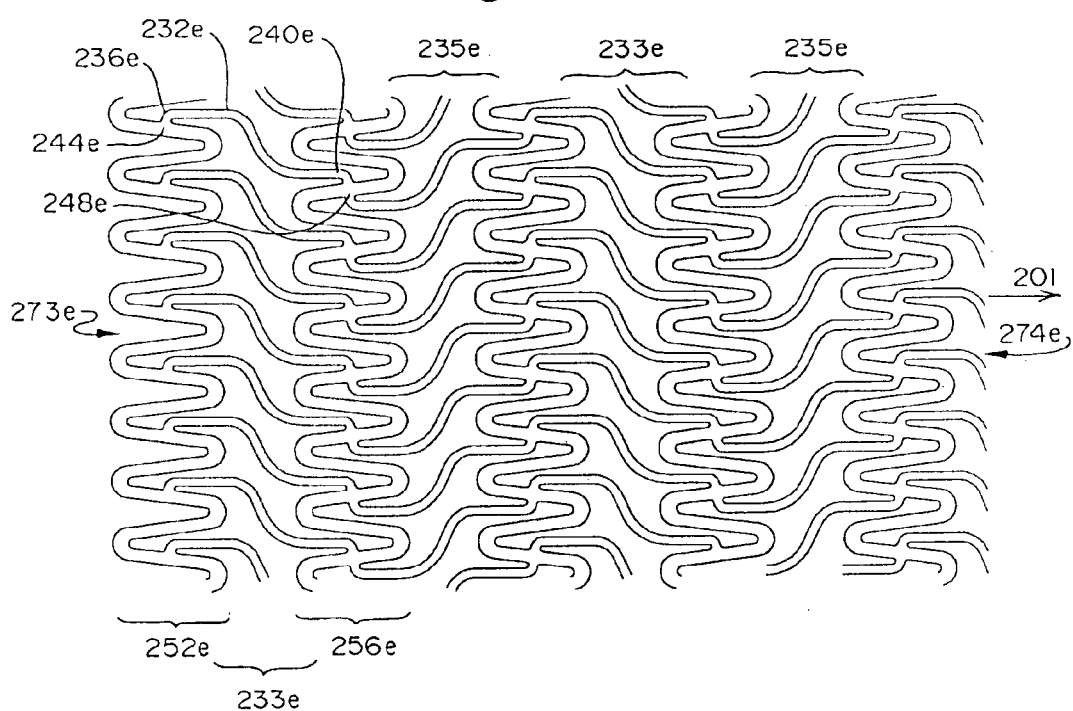
FIG. 4e shows a flat view of an alternate unexpanded stent configuration according to the invention.

FIGS. 4b–f show embodiments in which first and second shanks are oriented in substantially the same direction, as in FIG. 2, and in which the first and second shanks of a link are displaced circumferentially. In the embodiment shown in FIG. 4b, first shank 236b of each link 232b extends from a first region 244b on a first band-like element 252b and second shank 240b of each link 232b extends from a second region 248b on an adjacent band-like element 256b, with second region 248b situated opposite a region one wavelength further along first band-like element 252b from first region 244b. All links 232b are similarly oriented. In the embodiment shown in FIG. 4c, first shank 236c of each link 232c extends from a first region 244c on a first band-like element 252c and second shank 240c of each link 232c extends from a second region 248b on an adjacent band-like element 256c, with second region 248b situated opposite a region two wavelengths further along first band-like element 252c from first region 244c. As in FIG. 4b, all links 232c are similarly oriented. In the embodiment shown in FIG. 4d, first shank 236d of each link 232d extends from a first region 244d on a first band-like element 252d and second shank 240d of each link 232d extends from a second region 248d on an adjacent band-like element 256d, with second region 248d situated opposite a region one wavelength further along first band-like element 252d from first region 244d. FIG. 4d differs from FIG. 4b in that adjacent rows of links 233d and 235d are out of phase with one another in FIG. 4d where they are in phase in FIG. 4b. In the embodiment shown in FIG. 4e, first shank 236e of each link 232e extends from a first region 244e on a first band-like element 252e and second shank 240e of each link 232e extends from a second region 248e on an adjacent band-like element 256e, with second region 248e situated opposite a region one wavelength further along first band-like element 252e from first region 244e. As in FIG. 4d, adjacent rows of links 233e and 235e are out of phase with one another. It should also be noted that in the pattern in FIG. 4e, unlike in FIG. 4d, links 232e are seen to form a continuous path across the stent from first end 273e to second end 274e of the stent.

In the embodiment shown in FIG. 4f, first shank 236f of each link 232f extends from a first region 244f on a first band-like element 252f and second shank 240f of each link 232f extends from a second region 248f on an adjacent band-like element 256f, with second region 248f situated opposite a region one wavelength further along first band-like element 252f from first region 244f. Adjacent rows of links 233f and 235f are out of phase with one another. It should also be noted that in the pattern in FIG. 4f, links 232f are seen to form a continuous substantially helical path across the stent from first end 273f to second end 274f of the stent.

Figure 4G:
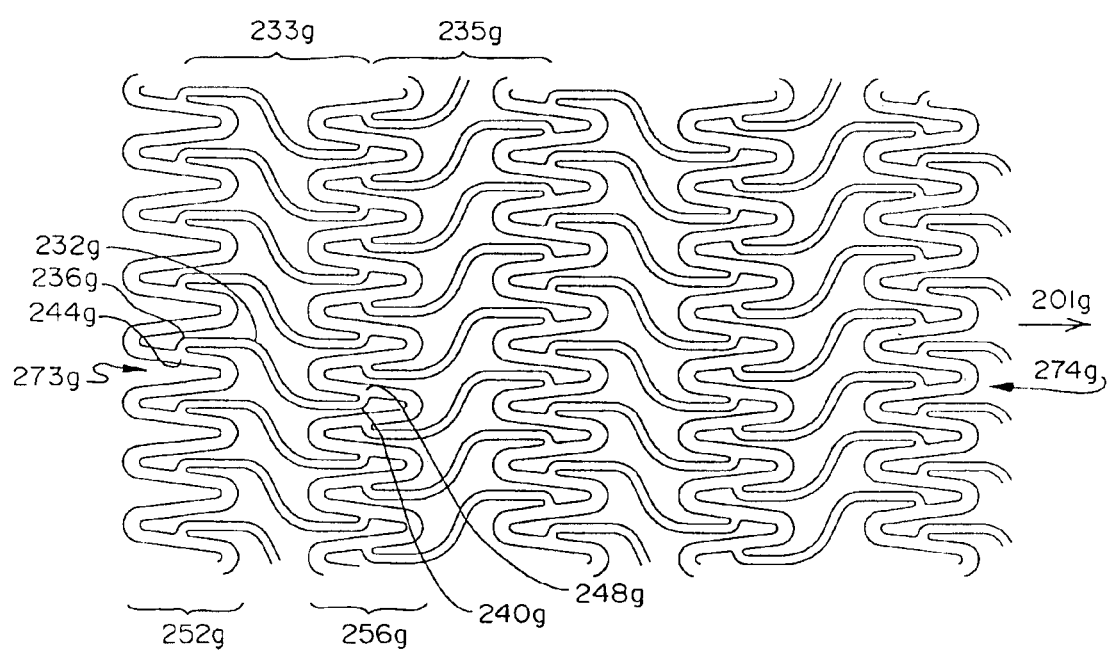
FIG. 4g shows a flat view of an alternate unexpanded stent configuration according to the invention.

In the embodiment shown in FIG. 4g, first shank 236g of each link 232g extends from a first region 244g on a first band-like element 252g and second shank 240g of each link 232g extends from a second region 248g on an adjacent band-like element 256g, with second region 248g situated opposite a region one-half wavelength further along first band-like element 252g from first region 244g. Adjacent rows of links 233g and 235g are out of phase with one another.

In the embodiment shown in FIG. 4h, first shank 236h of each link 232h extends from a first region 244h on a first band-like element 252h and second shank 240h of each link 232h extends from a second region 248h on an adjacent band-like element 256h, with second region 248h situated opposite a region one-half wavelength further along first band-like element 252h from first region 244h. Links in adjacent rows of links 233h and 235h are similarly oriented. It should also be noted that in the pattern in FIG. 4h, links 232h are seen to form a continuous helical path across the stent from first end 273h to second end 274h of the stent.

Figure 4I:
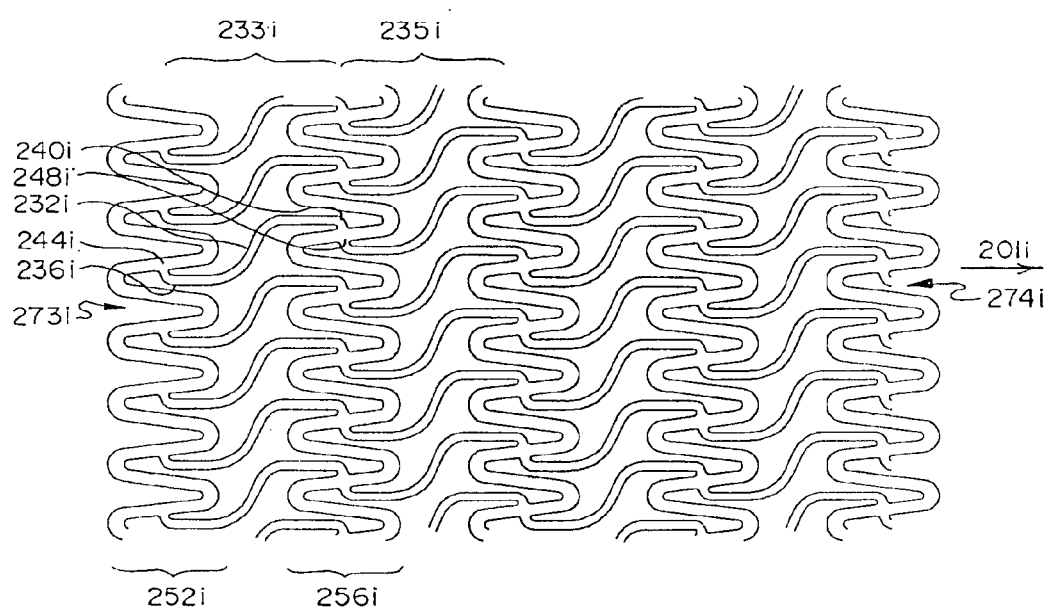
FIG. 4i shows a flat view of an alternate unexpanded stent configuration according to the invention.

Finally, FIG. 4i presents an embodiment which is a mirror image of the stent of FIG. 4h. First shank 236i of each link 232i extends from a first region 244i on a first band-like element 252i and second shank 240i of each link 232i extends from a second region 248i on an adjacent band-like element 256i, with second region 248i situated opposite a region one-half wavelength further along first band-like element 252i from first region 244i. Links in adjacent rows of links 233i and 235i are similarly oriented. It should also be noted that in the pattern in FIG. 4i, links 232i are seen to form a continuous helical path across the stent from first end 273i to second end 274i of the stent.

FIGS. 4g–i are similar to FIG. 4a in that one shank of a link is oriented upward and one shank of a link is oriented downward.

As in FIGS. 1–3, in the embodiments of FIGS. 4a–i, each band-like element consists of one sub-element and as such, the sub-element is indistinguishable from the band-like element. Further, as in the stent of FIGS. 1–3, the links in adjacent rows of links in FIGS. 4a and 4d are 180° out of phase with one another. In FIGS. 4b and 4c, on the other hand, the links in adjacent rows of links are in phase with one another.

The stent of FIG. 4a may also seen to be formed of a plurality of band-like elements 216a and a plurality of spaced generally longitudinal elements 272a (one of which is highlighted, for the sake of clarity). Longitudinal elements 272a extending from the first end 273a of the stent to the second end 274a of the stent and having alternating peaks 275a and troughs 276a and longitudinal transition regions 277a midway between adjacent peaks 275a and troughs 276a. Adjacent longitudinal elements 272a are in phase with one another. Each generally longitudinal element 272a intersects each band-like element 216a in a region of intersection 278a, the region of intersection including a region between a peak and a trough on a band-like element, and a transition region 277a of a longitudinal element 272a. Longitudinal elements 272a are seen to proceed across the stent in a generally diagonal fashion.

Figure 5:
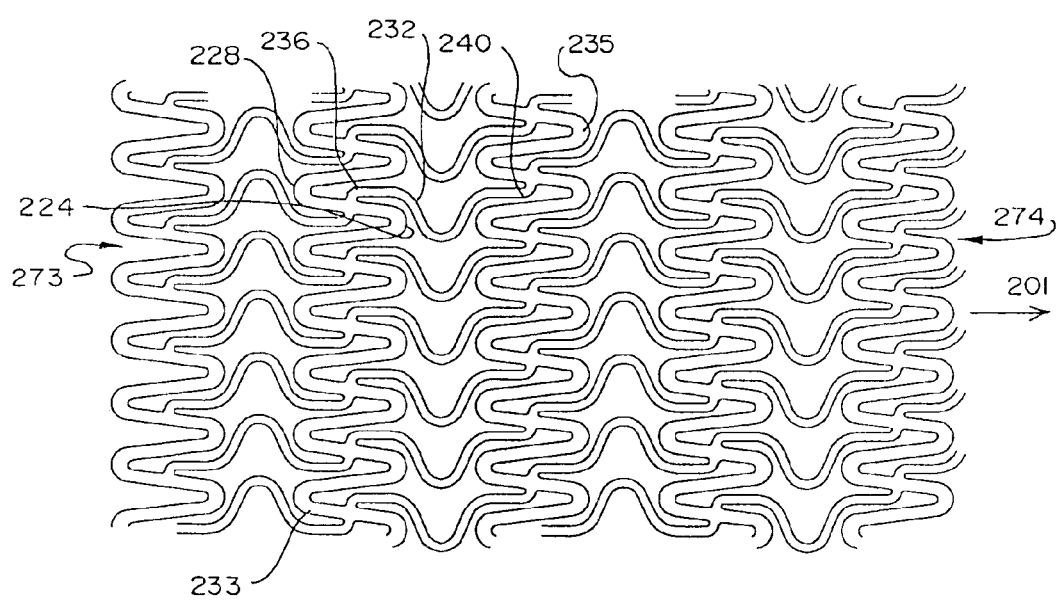

FIG. 5 shows an enlarged portion of the pattern shown in FIG. 4a. Link 232 extends from a region 233 on a band-like element substantially midway between a peak 224 and an adjacent trough 228 to a region 235 substantially midway between a peak 224 and an adjacent trough 228 on an adjacent band-like element.

Figure 6A:
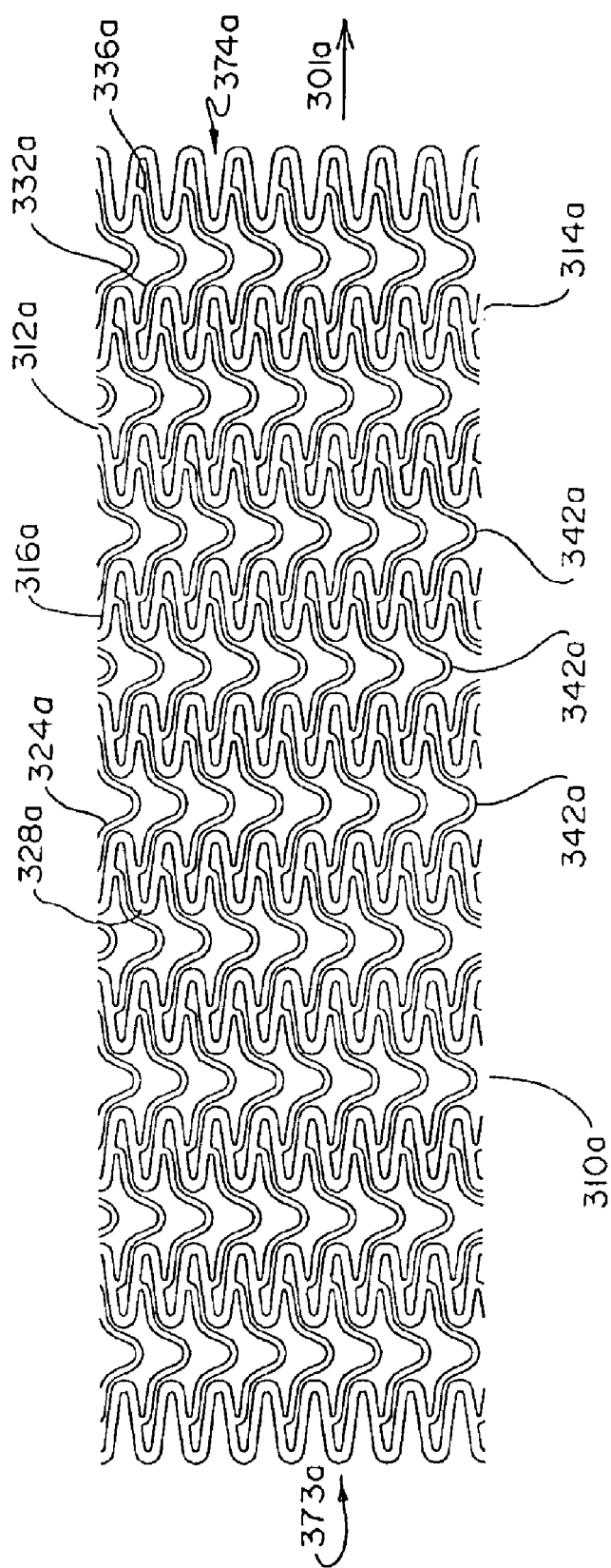
FIG. 6a shows a flat view of an alternate unexpanded stent configuration according to the invention.

In another embodiment, as shown generally at 310a in FIG. 6a, links in adjacent rows are in phase with one another. Links 332a extending between adjacent band-like elements 316a are arranged to form rows 342a of links 332a. The links, in this case, are all identically oriented. Of course, other arrangements are possible as well, such as alternating the phase of the links by 180 degrees every 'n'th row where n is an integer, or having a block of rows with the links oriented in one way followed by a block of rows with the links oriented in the opposite direction.

Figure 6B:
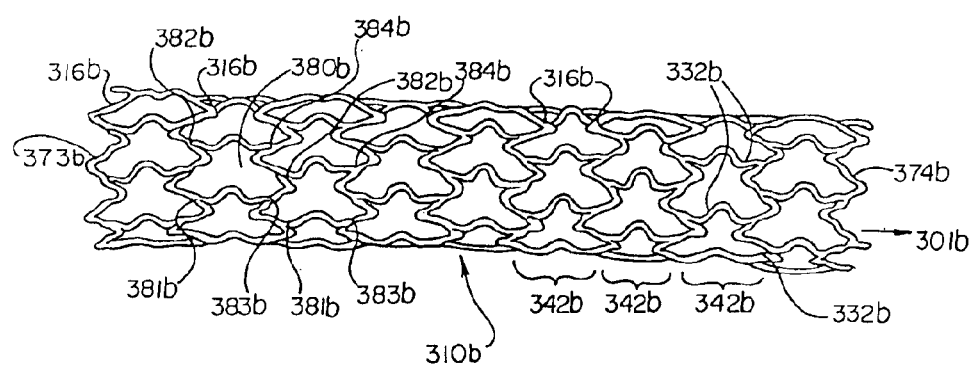

FIG. 6b shows a tubular stent formed with the pattern of FIG. 6a, after expansion. The stent, shown generally at 310b comprises links 332b extending between adjacent band-like elements 316b are arranged to form rows 342b of links 332b which are all identically oriented. The stent of FIG. 6b may also be seen to be formed of a plurality of interconnected cells 380b, each cell having a first corner 381b, a second corner 382b, a third corner 383b and a fourth corner 384b. The third and fourth corners of primary cells and the first and second corners of abutting primary cells in adjacent bands are displaced relative to one or another by half a primary cell so that as one traverses the stent from proximal end 373b to distal end 374b, the cells are staggered. As seen in FIG. 6b, each cell 380b is oriented in a direction substantially parallel to the longitudinal axis. Stated differently, links 332b which form the sides of cells 380b are oriented in a overall direction substantially parallel to the longitudinal axis minimizing torsional stresses within the stent.

Figure 6C:
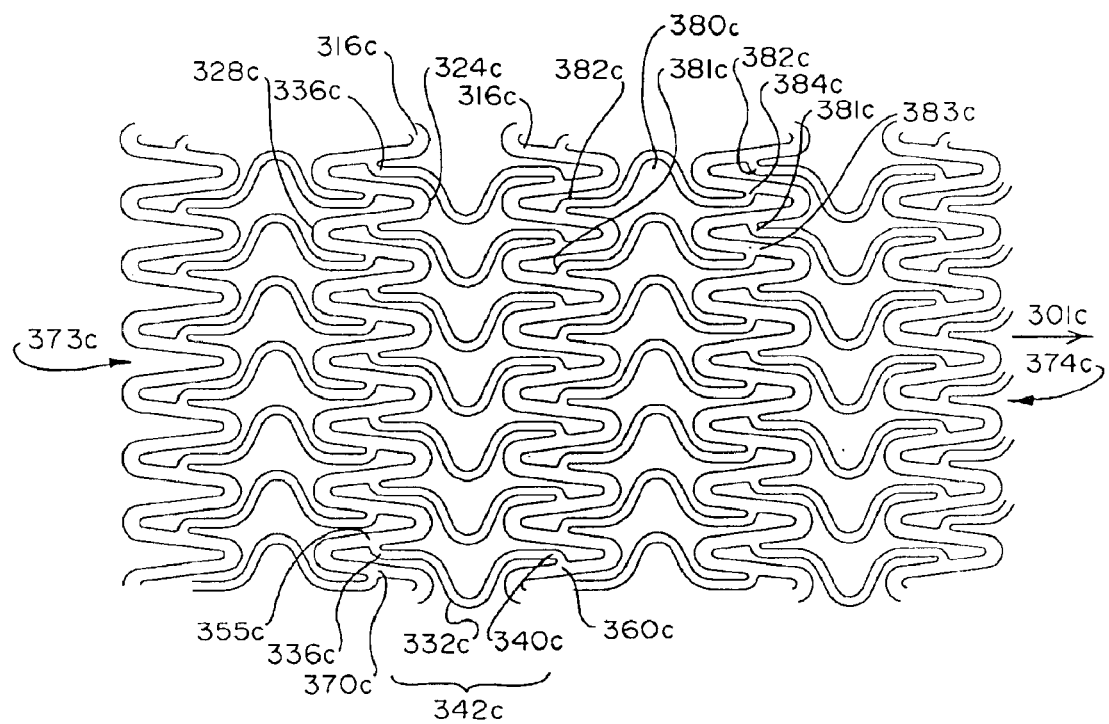
FIG. 6c shows a flat view of an alternate unexpanded stent configuration according to the invention.

In another embodiment, as shown in FIG. 6c, the stent, shown generally at 310c in flat pattern, is similar to the stent of FIG. 6a. The stent is formed of interconnected band-like elements 316c (in this embodiment the band-like element is identical to the sub-element, there being only one sub-element). Band-like elements 316c are wave-like, having peaks 324c and troughs 328c. Adjacent band-like elements 316c are interconnected by substantially 'U' shaped links 332c. The links 332c that interconnect a given set of adjacent band-like elements 316c form a row 342c. The stent is comprised of one or more of such rows. The stent of FIG. 6c differs, however, from the stent of FIG. 6a in two aspects. First, adjacent rows 342c of links 332c are 180° out of phase with one another. And second, the first shank 336c of each link 332c extends from a first region of intersection 355c on a band-like element 316c and the second shank 340c of each link 332c extends from a region of intersection 360c on an adjacent band-like element 316c, the region of intersection 360c on the adjacent band-like element 316c situated opposite a region 370c one half wavelength further along the first band-like element from the first region of intersection 355c.

The stent of FIG. 6c may also be seen to be formed of a plurality of interconnected cells 380c, each cell having a first corner 381c, a second corner 382c, a third corner 383c and a fourth corner 384c. The third and fourth corners of primary cells and the first and second corners of abutting primary cells in adjacent bands are displaced relative to one or another by half a primary cell so that as one traverses the stent from proximal end 373c to distal end 374c, the cells are staggered. Although not shown, the cells of a tubular stent formed according to the pattern of FIG. 6c, upon expansion of the stent are oriented in a direction which is skewed relative to the longitudinal axis of the stent, leading to torsional stresses within the stent.

Figure 7B:
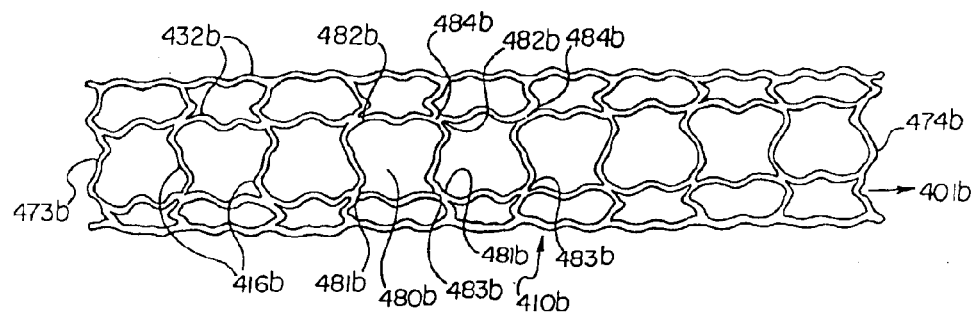
Figure 7A:
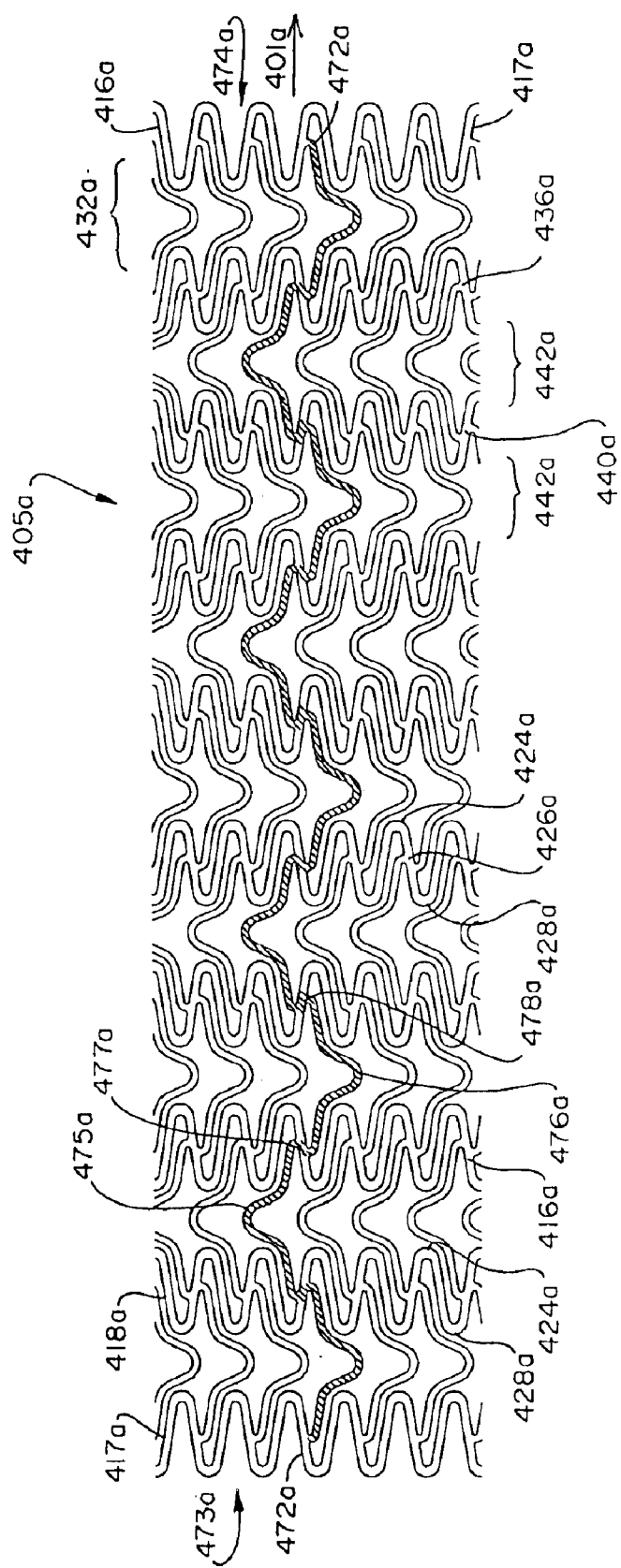
FIG. 7a shows a flat view of an alternate unexpanded stent configuration according to the invention.

In another embodiment, as shown in FIG. 7a, the stent in flat form, shown generally at 405a is seen to be made up of a plurality of spaced band-like elements, generally indicated at 416a consisting of one sub-element. In the present embodiment, the sub-element is identical to the band-like element. The stent comprises end band-like elements 417a located at either end of the stent and intermediate band-like elements 418a disposed between end band-like elements 417a. Each band-like element 416a has a generally serpentine configuration to provide continuous waves of generally sinusoidal character to each band-like element 416a, the waves being characterized by a plurality of peaks 424a and troughs 428a taking a generally longitudinal direction along the stent. As the stent is expanded from a first diameter to a second diameter, the waves in band-like elements open. The stent further comprises a plurality of substantially U-shaped links 432a connect adjacent band-like elements 416a together. Links 432a extending between adjacent band-like elements 416a are arranged to form rows 442a of links 432a. Links in adjacent rows are 180° out of phase with one another. Links 432a terminate in first 436a and second 440a shanks.

For each first shank 436a attached to an intermediate band-like element 418a between a peak 424a and a trough 428a, there is a second shank 440a across the intermediate band-like element 418a and displaced from first shank 436a and located between the same peak and trough as is first shank 436a. First shanks 436a attached to any given band-like element 416a are spaced substantially one wavelength apart along the band-like element and similarly, second shanks 440a attached to any given band-like element 416a are spaced substantially one wavelength apart along the band-like element.

The stent of FIG. 7a may also seen to be formed of a plurality of band-like elements 416a and a plurality of spaced generally longitudinal elements 472a (one of which is highlighted for the sake of clarity). Longitudinal elements 472a extending from the first end 473a of the stent to the second end 474a of the stent and having alternating peaks 475a and troughs 476a and longitudinal transition regions 477a midway between adjacent peaks 475a and troughs 476a. Adjacent longitudinal elements 472a are in phase with one another. Each generally longitudinal element 472a intersects each band-like element 416a in a region of intersection 478a, the region of intersection including a region between a peak and a trough on a band-like element, and a transition region 477a of a longitudinal element 472a.

FIG. 7b shows a tubular stent generally at 410b, the stent formed of the configuration of FIG. 7a, in expanded form. The expanded stent is seen to comprise band-like elements 416b joined together by links 432b. Links 432b correspond to the substantially U-shaped links 432*a* of the unexpanded stent and are seen to open upon expansion of the stent.

In the expanded form, the stent can also clearly be seen to comprise a plurality of interconnected cells 480*b*, each cell having a first corner 481*b*, a second corner 482*b*, a third corner 483*b* and a fourth corner 484*b*. Links 432*b* forming the sides of cells 480*b* are seen to be substantially parallel to the longitudinal axis. As such, each cell is substantially aligned in the longitudinal direction. The third and fourth corners of primary cells and the first and second corners of abutting primary cells in adjacent bands are displaced only slightly relative to one or another so that as one traverses the stent from proximal end 473*b* to distal end 474*b*, the progression of cells from one end to the other end is slightly skewed relative to the longitudinal axis of the stent due to an artifact associated with the expansion of the balloon used to expand the stent.

In another embodiment shown in FIG. 8 the stent, shown generally at 510, is similar to the stent of FIG. 6*c*, differing, however, in one aspect. Links 532 connecting adjacent band-like elements 516 are zig-zag shaped. As with the stent of FIG. 7, the phase of links 532 in adjacent rows 542 differs by 180°. Similarly, first shanks 536 and second shanks 540 are separated by a half of a wavelength along each of the intermediate band-like elements 517. Intermediate band-like elements are defined as the band-like elements between the first band-like element 516 in the stent and the final band-like element 516 in the stent.

The stent of FIG. 8 is also seen to be formed of primary cells 580 consisting of first member 581 and second member 584 joined together by first link 587 and second link 590. First link 587 and second link 590 are seen to be parallel.

Figure 9:
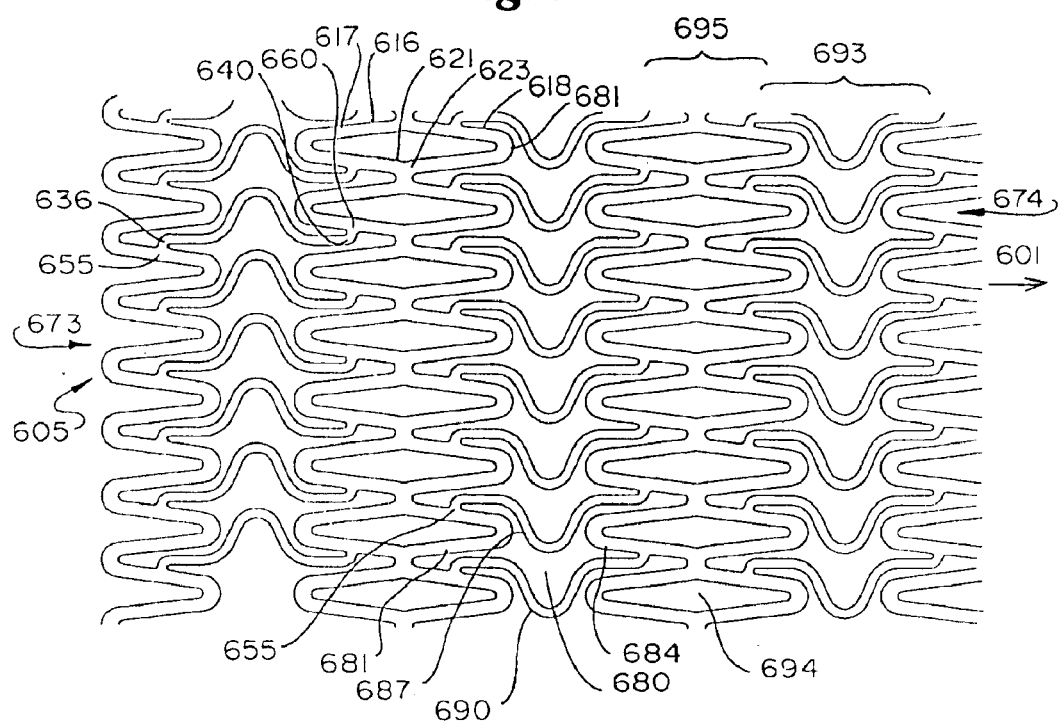
FIG. 9 shows a flat view of an alternate unexpanded stent configuration according to the invention.

In yet another embodiment shown in FIG. 9, the stent in flat form, shown generally at 605 is seen to be made up of a plurality of spaced band-like elements, 616 consisting of two interconnected sub-elements 617 and 618. Each sub-element 617 and 618 has a generally serpentine configuration. Sub-elements 617 and 618 are arranged 180° out of phase relative to one another, peaks 621 of first sub-elements 617 connected to troughs 623 of second sub-elements 618 so as to form band-like elements 616. Adjacent band-like elements 616 are in phase with one another and are interconnected by "U" shaped links 632. As with the stent of FIG. 6*b*, the first shank 636 of each link 632 extends from a first region of intersection 655 on a band-like element 616 and the second shank 640 of each link 632 extends from a region of intersection 660 on an adjacent band-like element 616, the region of intersection 660 on the adjacent band-like element 616 situated opposite a region 670 one half wavelength (based on the wavelength of the band-like element) further along the first band-like element from the first region of intersection 655.

The stent of FIG. 9 is also seen to be formed of primary cells 680 consisting of first member 681 and second member 684 joined together by first link 687 and second link 690. First link 687 and second link 690 are seen to be parallel. Primary cells 680 are arranged in primary bands shown generally at 693 and are interconnected with diamond shaped secondary cells 694, arranged in secondary bands, shown generally at 695. Primary 693 and secondary bands 694 alternate along the length of the stent.

Figure 10:
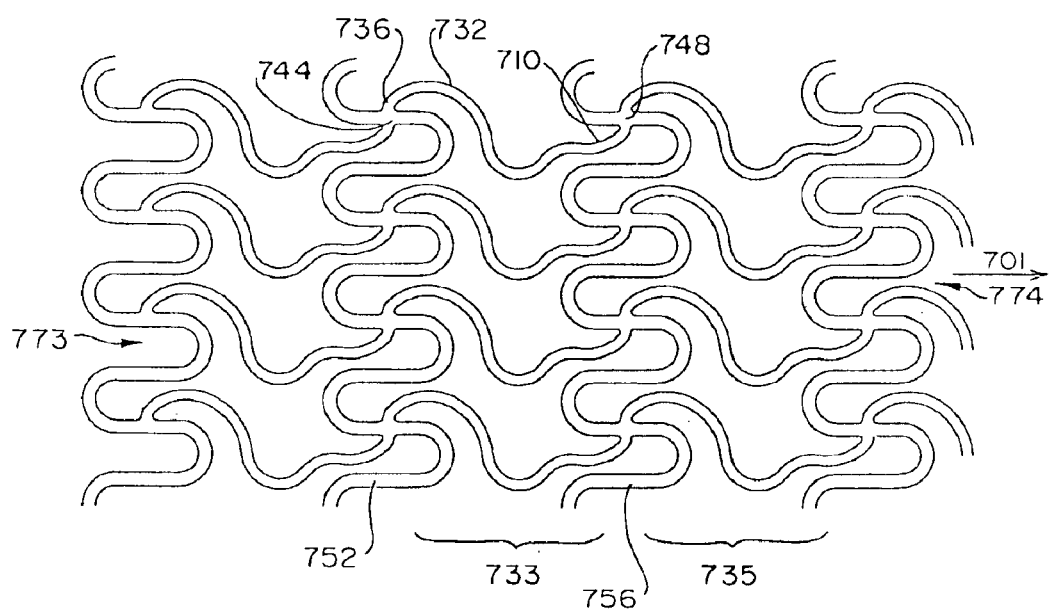
FIG. 10 shows a flat view of an alternate unexpanded stent configuration according to the invention.

While adjacent band-like elements are depicted in FIGS. 1–9 as being out of phase with one another by 180°, adjacent band-like elements may be in phase, as shown in FIG. 10–14 or may have their phases differ by intermediate amounts. FIG. 10 shows a portion of an inventive stent in the flat. As seen in FIG. 10, first shank 736 of each link 732 extends from a first region 744 on a first band-like element 752 and second shank 740 of each link 732 extends from a second region 748 on an adjacent band-like element 756, with second region 748 situated substantially opposite first region 744. First shanks 736 and second shanks 740 of each link 732, however, are oppositely oriented. Links in adjacent rows of links 733 and 735 are similarly oriented. It should also be noted that in the pattern in FIG. 10, links 732 are seen to form a continuous path across the stent from first end 773 to second end 774 of the stent.

Figure 11:
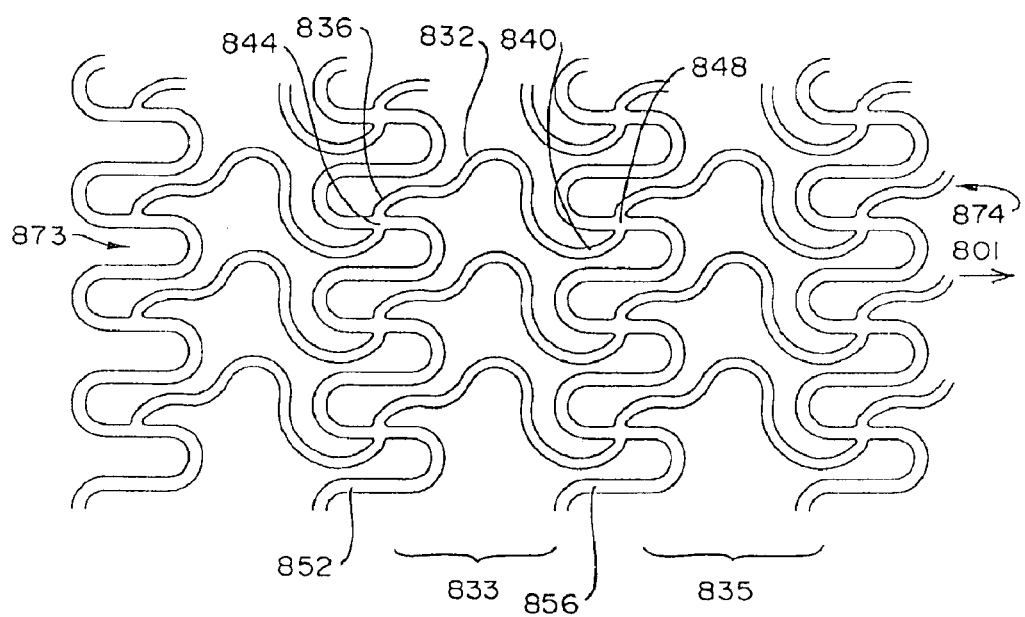
FIG. 11 shows a flat view of an alternate unexpanded stent configuration according to the invention.

FIG. 11 shows a portion of an inventive stent in the flat. As seen in FIG. 11, first shank 836 of each link 832 extends from a first region 844 on a first band-like element 852 and second shank 840 of each link 832 extends from a second region 848 on an adjacent band-like element 856, with second region 848 situated substantially opposite first region 844. First shanks 836 and second shanks 840 of each link 832, however, are oppositely oriented. Links in adjacent rows of links 833 and 835 are similarly oriented. It should also be noted that in the pattern in FIG. 11, links 832 are seen to form a continuous path across the stent from first end 873 to second end 874 of the stent.

Figure 12:
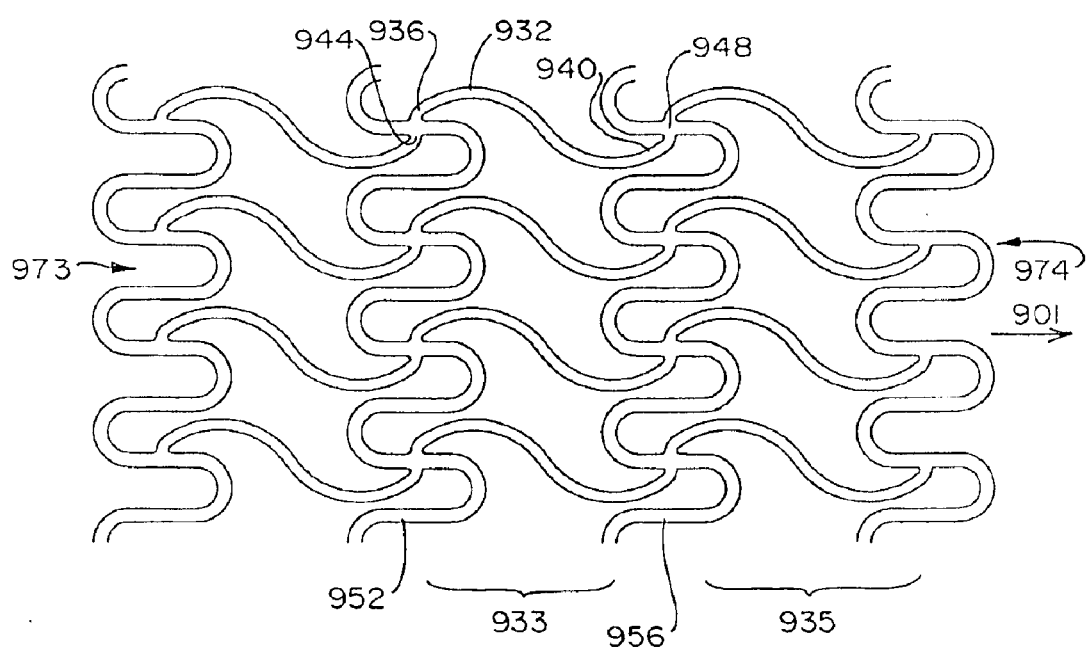
FIG. 12 shows a flat view of an alternate unexpanded stent configuration according to the invention.

FIG. 12 shows a portion of an inventive stent in the flat. As seen in FIG. 12, first shank 936 of each link 932 extends from a first region 944 on a first band-like element 952 and second shank 940 of each link 932 extends from a second region 948 on an adjacent band-like element 956, with second region 948 situated substantially opposite first region 944. First shanks 936 and second shanks 940 of each link 932, however, are oppositely oriented. Links in adjacent rows of links 933 and 935 are similarly oriented. It should also be noted that in the pattern in FIG. 12, links 932 are seen to form a continuous path across the stent from first end 973 to second end 974 of the stent.

Figure 13:
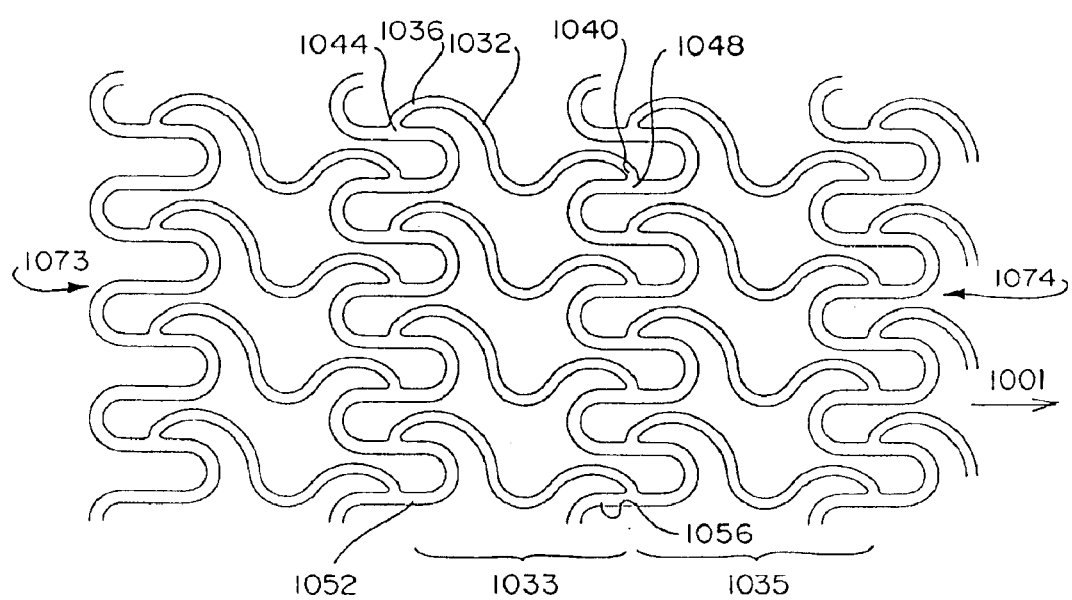
FIG. 13 shows a flat view of an alternate unexpanded stent configuration according to the invention.

FIG. 13 shows a portion of an inventive stent in the flat. As seen in FIG. 13, first shank 1036 of each link 1032 extends from a first region 1044 on a first band-like element 1052 and second shank 1040 of each link 1032 extends from a second region 1048 on an adjacent band-like element 1056, with second region 1048 situated substantially opposite first region 1044. First shanks 1036 and second shanks 1040 of each link 1032 are similarly oriented but displaced circumferentially by about one-half wavelength along band-like elements 1052 and 1056. Links in adjacent rows of links 1033 and 1035 are out of phase with one another.

Figure 14:
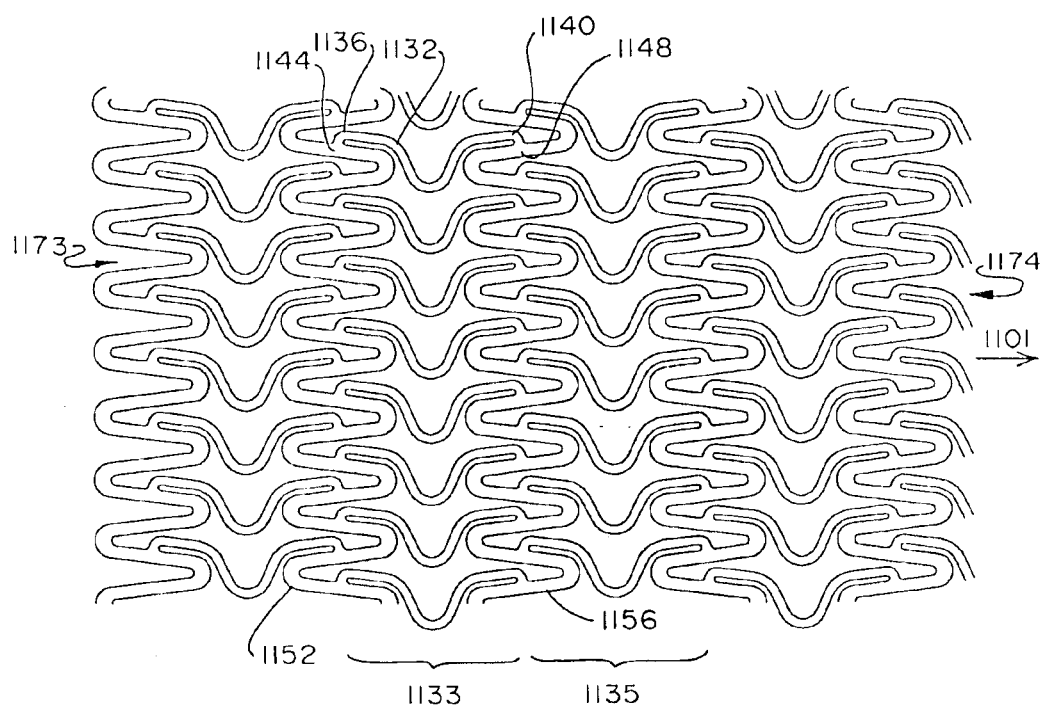
FIG. 14 shows a flat view of an alternate unexpanded stent configuration according to the invention.

FIG. 14 shows a portion of an inventive stent in the flat. As seen in FIG. 14, first shank 1136 of each link 1132 extends from a first region 1144 on a first band-like element 1152 and second shank 1140 of each link 1132 extends from a second region 1148 on an adjacent band-like element 1156, with second region 1148 situated substantially opposite first region 1144. First shanks 1136 and second shanks 1140 of each link 1132 are similarly oriented. Links in adjacent rows of links 1133 and 1135 are similarly oriented.

Although FIGS. 1–9 show a one to one correspondence between peaks and links, in a more general sense, fewer links may be used. For example, there may be one link for every two peaks. There must, however, be at least one link between every two adjacent bands. Stated differently, while in the embodiments shown in the figures the links are separated by one wavelength along the band-like elements, separations of greater than a wavelength including integral and non-integral wavelength separations are contemplated. As such, the number of links between any two adjacent bands will range from one link to the number of multiples of a wavelength that are present in the band-like element. Similarly the number of spaced generally longitudinal elements may range from one to the number of multiples of a wavelength that are present in the band-like element.

Further, while it is preferable for the band-like elements to be evenly spaced apart, it is not necessary. In the case where the bands are not evenly spaced, that is, different sets of adjacent bands are separated by different distances, the links may have differing wingspans (i.e. the distance from first shank to second shank). Moreover, even where the bands are evenly spaced apart, the links may have differing wingspans depending on where the shanks intersect the band-like elements.

It is understood that the present invention also contemplates substituting 'U' shaped links for zig-zag shaped links and vice versa as well as links with one or more bends therein. As such, the links shown in the various figures are all interchangeable, allowing for minor modifications to allow for the requisite orientation of the shanks. Preferably, the links will exhibit a degree of flexibility, thereby contributing to the overall flexibility of the cells.

Figure 15:
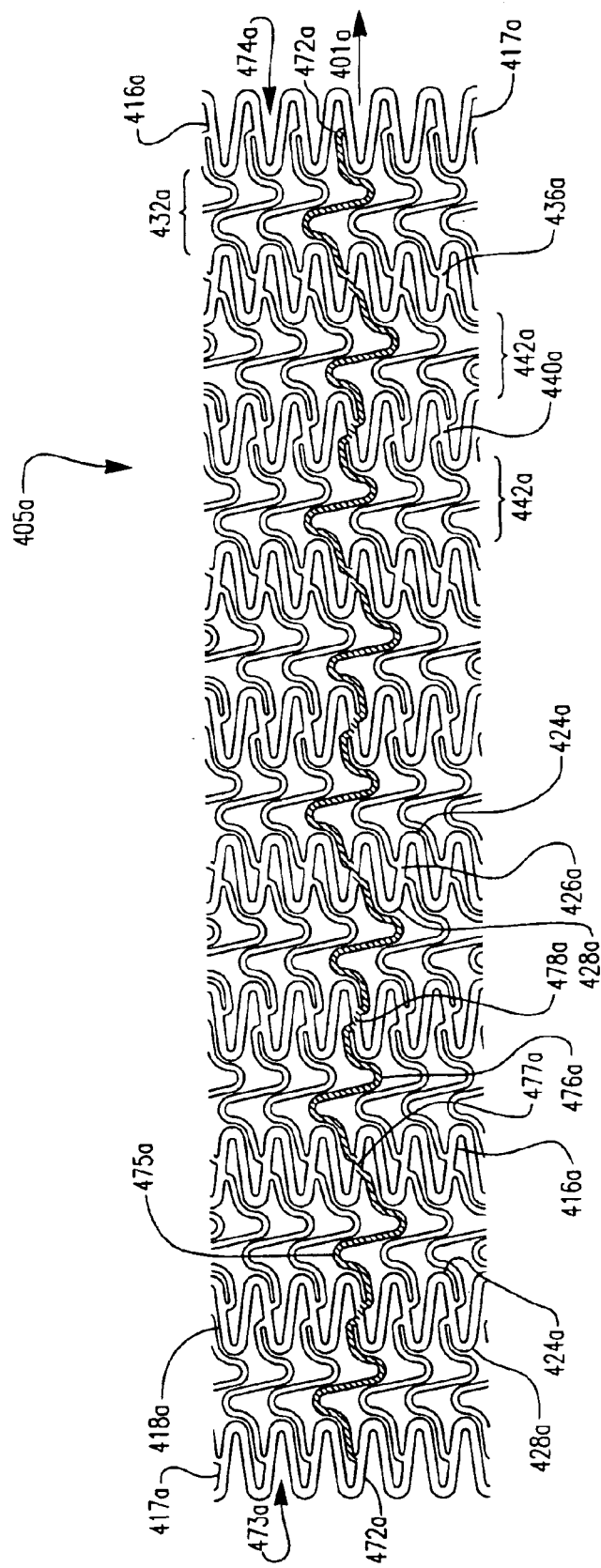
FIG. 15 shows a flat view of an alternate unexpanded stent configuration according to the invention.

For example, in the embodiment depicted in FIG. 15. the stent 405a is shown having band-like elements 416a in a conflauration similar to that of the stent previously depicted in FIG. 7a. Each of the substantially U-shaped links 432a are provided with an additional bend such as in the manner shown of the links 532 in FIG. 8 and/or the links 932 of FIG. 12.

Figure 16:
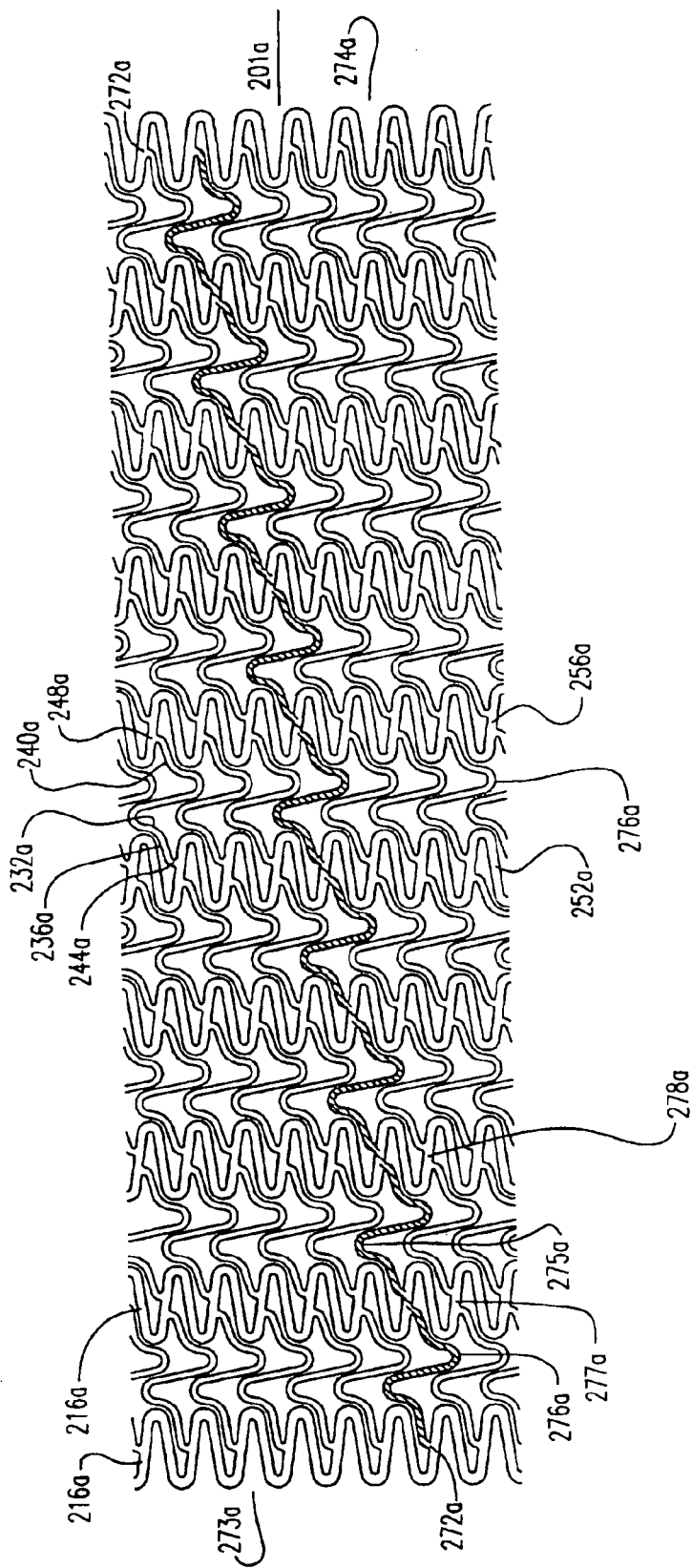
FIG. 16 shows a flat view of an alternate unexpanded stent configuration according to the invention.
Figure 4B:
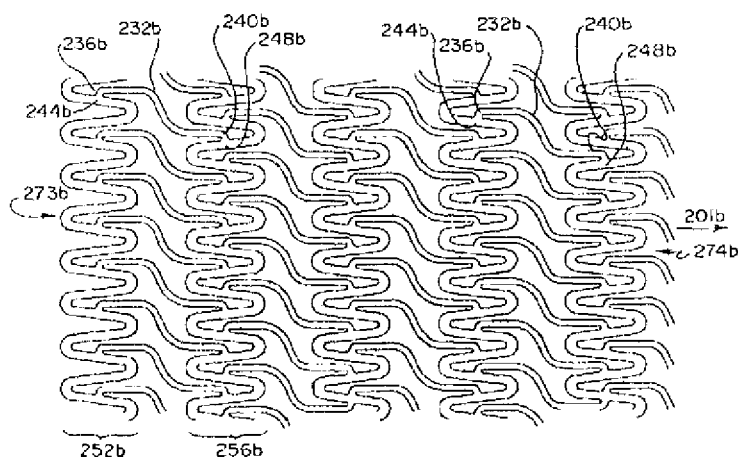

In another example a stent configuration is shown in FIG. 16 wherein the longitudinal element 272a, such as previously shown in FIG. 4A, is made up of links similar to those depicted in FIG. 15. As such, the stent of FIG. 16 may also be formed of a plurality of band-like elements 216a and a plurality of spaced generally longitudinal elements 272a (one of which is highlighted, for the sake of clarity). Longitudinal elements 272a extending from the first end 273a of the stent to the second end 274a of the stent and having alternating peaks 275a and troughs 276a and longitudinal transition regions 277a midway between adjacent peaks 275a and troughs 276a. Each generally longitudinal element 272a intersects each band-like element 216a in a region of intersection 278a, the region of intersection including a region between a peak and a trough on a band-like element, and a transition region 277a of a longitudinal element 272a. Longitudinal elements 272a are proceed across the stent in a generally diagonal fashion in a manner similar to those shown in FIG. 4A.

Although most of the figures show the inventive stents in the flat for clarity, it is understood that the stents may be formed into as tubular shape by rolling the flat patterns shown about the longitudinal axis so as to bring the edges and together, as shown in FIG. 2. The edges may then be joined as by welding or the like to provide a configuration such as that showed in FIG. 2. The stents may also be formed of a laser-cut tube.

The invention further contemplates a radially expandable stent having first and second ends and comprising a plurality of spaced band-like elements forming a hollow cylinder, and a plurality of spaced generally longitudinal elements intersecting the bands and extending from one end of the stent to the other. The band-like elements are arranged sequentially along the cylinder. Each band-like element has a generally serpentine configuration to provide continuous waves of generally sinusoidal character to each band-like element. The waves are characterized by a plurality of peaks and troughs taking a generally longitudinal direction along the cylinder. Midway between the peaks and troughs is a midpoint region. Preferably, adjacent bands will be out of phase with each other by 180°.

The plurality of spaced generally longitudinal elements have alternating peaks and troughs and longitudinal transition regions midway between adjacent peaks and troughs. Each generally longitudinal element intersects each band like element in a region of intersection which includes a transition region of a longitudinal element and a midpoint region of a band. Each generally longitudinal element may, but need not be substantially perpendicular to each band like element in each region of intersection in the unexpanded stent. The longitudinal transition region of the longitudinal elements may be zig-zag shaped or substantially 'S' shaped.

The inventive stents are also designed so as to have desired shortening or lengthening characteristics upon radial expansion. The exact shortening or lengthening characteristics will depend on the placement of the shanks relative to the midpoint positions on the band-like elements between adjacent peaks and troughs. The midpoint position is defined to be the position midway between an adjacent peak and trough on a band-like element. One such midpoint is designated by numeral 126 in FIG. 1. When the first shank of each link is attached to a band-like element between a midpoint and a peak (i.e. closer to a peak than to a trough) and the second shank of each link is attached to a band-like element between a midpoint and a trough (i.e. closer to a trough than to a peak), the stent is expected to shorten as the links are placed in tension on expansion of the stent. If, on the other hand, the first shank of each link is attached to a band-like element between a midpoint 426a and a trough 428a and the second shank of each link is attached to a band-like element between a midpoint 426a and a peak 424a, as in FIG. 7a, the stent is expected to lengthen as the links are placed in compression on expansion of the stent. Of course, the exact lengthening or shortening characteristics will depend on other properties as well such as the material and construction including dimensions, geometry, morphology, configuration, functional behavior and mechanical behavior of the stent and in particular, the links.

Although all of the stents, with the exception of that shown in FIGS. 7a and 7b, are shown with links emanating from midway between the peak region and the trough region of the band-like element, the invention contemplates the possibility of links emanating from anywhere between the peak and the trough region of a band so as to control shortening and lengthening characteristics of the stent.

As already indicated, this invention is applicable to self-expanding configurations, mechanically expandable configurations and to stents made of a wide variety of materials, including metal, plastic and any other material capable of functioning as an expandable stent. For example, the stent may be of metal wire or ribbon such as tantalum, stainless steel or the like or of metal sheeting or metal tubing. It may be thin-walled. It may be of shape memory alloy such as Nitinol or the like.

The figures disclosed herein are not intended to be limited to the stents shown but are further intended to convey equivalent structures such as stents which are the mirror images of an embodiment, and stents whose patterns may derived from the patterns shown here via a variety of symmetry operations such as reflections, rotations and inversions and combinations thereof about a given point, line or plane, as well as other equivalent structures.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent comprising a plurality of serpentine segments which form closed paths, the serpentine segments having alternating peaks and troughs, serpentine segments which are adjacent one another connected by a plurality of connectors, each connector having a first end which extends from a first position offset from midway between a peak and a trough on one serpentine segment the first position being closer to midway between the peak and the trough than to the peak, a second end which extends from a second position offset from midway between a peak and a trough on an adjacent serpentine segment, the second position being closer to midway between the peak and the trough than to the trough, and a central region between the first and second ends, at least a portion of each central region comprising a first U-shaped link and a second U-shaped link, each first U-shaped link opening in a first substantially circumferential direction and each second U-shaped link opening in a second substantially circumferential direction substantially opposite the first substantially circumferential direction, at least a portion of the first U-shaped link and at least a portion of the second U-shaped link having a shared portion, the shared portion disposed between one of the peaks on one segment and one of the troughs on an adjacent segment.

2. The stent of claim 1 wherein each peak of a serpentine band is substantially longitudinally aligned with a trough of an adjacent serpentine band.

3. The stent of claim 2 wherein the connectors and portions of the serpentine band are arranged to form substantially helical pathways along the stent.

4. The stent of claim 1 wherein the connectors and portions of the serpentine bands are arranged to form substantially helical pathways along the stent, each portion extending in a region between a peak and a trough which is bounded by two connectors.

5. A stent comprising a plurality of serpentine segments which form closed paths, and a plurality of connectors connecting the serpentine segments, each connector comprising a first bend and a second bend, the first and second bends oriented in substantially opposite directions, each serpentine segment comprising a plurality of peaks and troughs, the serpentine segments and connectors arranged to form a plurality of helical pathways extending along the stent, each helical pathway extending along a plurality of successive connectors, successive connectors joined together by a portion of a serpentine segment, the portion extending from a first position along a serpentine segment to a second position along a serpentine segment, the first and second positions located between one trough and one peak, the first and second positions being closer to a midpoint between the peak and the trough than to the peak and trough, the portion traversing the midpoint.

6. The stent of claim 5 wherein each peak of a serpentine band is substantially longitudinally aligned with a trough of an adjacent serpentine band.

7. The stent of claim 5 wherein the first bend and the second bend are each substantially U-shape.

* * * * *

UNITED STATES PATENT AND TRADEMARK OFFICE
CERTIFICATE OF CORRECTION

PATENT NO. : 6,945,993 B2  Page 1 of 2
APPLICATION NO. : 10/287286
DATED : September 20, 2005
INVENTOR(S) : Graig L. Kveen, Timothy G. J. Ehr and Brian J. Brown It is certified that error appears in the above-identified patent and that said Letters Patent is hereby corrected as shown below:

In the drawings, Sheet 5, Fig. 4b, please replace with originally filed Fig. 4b.

Signed and Sealed this

Nineteenth Day of October, 2010

David J. Kappos
*Director of the United States Patent and Trademark Office*